(12) United States Patent
Thacker et al.

(10) Patent No.: US 9,278,215 B2
(45) Date of Patent: Mar. 8, 2016

(54) SELECTIVE HIGH FREQUENCY SPINAL CORD MODULATION FOR INHIBITING PAIN, INCLUDING CEPHALIC AND/OR TOTAL BODY PAIN WITH REDUCED SIDE EFFECTS, AND ASSOCIATED SYSTEMS AND METHODS

(71) Applicant: Nevro Corporation, Menlo Park, CA (US)

(72) Inventors: James R. Thacker, Homer, AK (US); Konstantinos Alataris, Belmont, CA (US); Bradford Evan Gliner, Sammamish, WA (US)

(73) Assignee: Nevro Corporation, Redwood City, CA (US)

( * ) Notice: Subject to any disclaimer, the term of this patent is extended or adjusted under 35 U.S.C. 154(b) by 0 days.

(21) Appl. No.: 13/831,241

(22) Filed: Mar. 14, 2013

(65) Prior Publication Data

US 2013/0261695 A1    Oct. 3, 2013

Related U.S. Application Data

(63) Continuation of application No. 13/607,617, filed on Sep. 7, 2012.

(60) Provisional application No. 61/532,523, filed on Sep. 8, 2011, provisional application No. 61/568,135, filed on Dec. 7, 2011.

(51) Int. Cl.
*A61N 1/36* (2006.01)
*A61N 1/05* (2006.01)

(52) U.S. Cl.
CPC .......... *A61N 1/36071* (2013.01); *A61N 1/0551* (2013.01); *A61N 1/0558* (2013.01); *A61N 1/36075* (2013.01); *A61N 1/36171* (2013.01); *A61N 1/36185* (2013.01)

(58) Field of Classification Search
CPC ............ A61N 1/3605; A61N 1/36071; A61N 1/36171; A61N 1/36175; A61N 1/3615; A61N 1/36157
USPC .......................................................... 607/46
See application file for complete search history.

(56) References Cited

U.S. PATENT DOCUMENTS 1,597,061 A    8/1926    Cultra
2,622,601 A    12/1952   Nemec
(Continued)

FOREIGN PATENT DOCUMENTS

DE    10318071 A1    11/2004
EP    1181947        2/2002
(Continued)

OTHER PUBLICATIONS

U.S. Appl. No. 13/607,617, filed Sep. 7, 2012, Thacker.
(Continued)

*Primary Examiner* — Eric D. Bertram
(74) *Attorney, Agent, or Firm* — Perkins Coie LLP

(57) ABSTRACT

Selective high-frequency spinal cord modulation for inhibiting pain with reduced side affects and associated systems and methods are disclosed. In particular embodiments, high-frequency modulation in the range of from about 1.5 KHz to about 100 KHz may be applied to the patient's spinal cord region to address neck or brachial plexus pain without creating paresthesia in the patient.

29 Claims, 18 Drawing Sheets

(56) References Cited

U.S. PATENT DOCUMENTS

| | | |
|---|---|---|
| 3,195,540 A | 7/1965 | Waller |
| 3,817,254 A | 6/1974 | Maurer |
| 3,822,708 A | 7/1974 | Zilber |
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,414,986 A | 11/1983 | Dickhudt et al. |
| 4,535,777 A | 8/1985 | Castel |
| 4,541,432 A | 9/1985 | Molina-Negro et al. |
| 4,608,985 A | 9/1986 | Crish et al. |
| 4,649,935 A | 3/1987 | Charmillot et al. |
| 4,764,132 A | 8/1988 | Stutz, Jr. |
| 4,841,973 A | 6/1989 | Stecker |
| RE33,420 E | 11/1990 | Sussman et al. |
| 5,002,053 A | 3/1991 | Garcia-Rill et al. |
| 5,335,657 A | 8/1994 | Terry, Jr. et al. |
| 5,354,320 A | 10/1994 | Schaldach et al. |
| 5,514,175 A | 5/1996 | Kim et al. |
| 5,562,717 A | 10/1996 | Tippey et al. |
| 5,643,330 A | 7/1997 | Holsheimer et al. |
| 5,716,377 A | 2/1998 | Rise |
| 5,776,170 A | 7/1998 | MacDonald et al. |
| 5,830,151 A | 11/1998 | Hadzic et al. |
| 5,853,373 A | 12/1998 | Griffith et al. |
| 5,893,883 A | 4/1999 | Torgerson et al. |
| 5,938,690 A | 8/1999 | Law |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feler et al. |
| 6,104,957 A | 8/2000 | Alo et al. |
| 6,161,044 A | 12/2000 | Silverstone |
| 6,167,311 A | 12/2000 | Rezai |
| 6,176,242 B1 | 1/2001 | Rise |
| 6,233,488 B1 | 5/2001 | Hess |
| 6,238,423 B1 | 5/2001 | Bardy |
| 6,246,912 B1 | 6/2001 | Sluijter et al. |
| 6,319,241 B1 | 11/2001 | King et al. |
| 6,341,236 B1 | 1/2002 | Osorio et al. |
| 6,356,786 B1 | 3/2002 | Rezai et al. |
| 6,393,325 B1 | 5/2002 | Mann et al. |
| 6,397,108 B1 | 5/2002 | Camps et al. |
| 6,405,079 B1 | 6/2002 | Ansarinia |
| 6,421,566 B1 | 7/2002 | Holsheimer |
| 6,440,090 B1 | 8/2002 | Schallhorn |
| 6,505,078 B1 | 1/2003 | King et al. |
| 6,510,347 B2 | 1/2003 | Borkan |
| 6,516,227 B1 | 2/2003 | Meadows et al. |
| 6,571,127 B1 | 5/2003 | Ben-Haim et al. |
| 6,584,358 B2 | 6/2003 | Carter et al. |
| 6,609,030 B1 | 8/2003 | Rezai et al. |
| 6,622,048 B1 | 9/2003 | Mann et al. |
| 6,659,968 B1 | 12/2003 | McClure |
| 6,714,822 B2 | 3/2004 | King et al. |
| 6,721,603 B2 | 4/2004 | Zabara et al. |
| 6,795,737 B2 | 9/2004 | Gielen et al. |
| 6,871,090 B1 | 3/2005 | He et al. |
| 6,885,888 B2 | 4/2005 | Rezai |
| 6,907,295 B2 | 6/2005 | Gross et al. |
| 6,923,784 B2 | 8/2005 | Stein |
| 6,928,230 B2 | 8/2005 | Squibbs |
| 6,928,320 B2 | 8/2005 | King |
| 6,950,707 B2 | 9/2005 | Whitehurst |
| 6,968,237 B2 | 11/2005 | Doan et al. |
| 6,990,376 B2 | 1/2006 | Tanagho et al. |
| 7,024,246 B2 | 4/2006 | Acosta et al. |
| 7,047,079 B2 | 5/2006 | Erickson |
| 7,082,333 B1 | 7/2006 | Bauhahn et al. |
| 7,117,034 B2 | 10/2006 | Kronberg |
| 7,146,224 B2 | 12/2006 | King |
| 7,149,574 B2 | 12/2006 | Yun et al. |
| 7,167,750 B2 | 1/2007 | Knudson et al. |
| 7,174,215 B2 | 2/2007 | Bradley |
| 7,177,702 B2 | 2/2007 | Wallace et al. |
| 7,180,760 B2 | 2/2007 | Varrichio et al. |
| 7,212,865 B2 | 5/2007 | Cory |
| 7,225,035 B2 | 5/2007 | Brabec et al. |
| 7,236,822 B2 | 6/2007 | Dobak, III |
| 7,239,912 B2 | 7/2007 | Dobak, III |
| 7,251,529 B2 | 7/2007 | Greenwood-Van Meerveld |
| 7,252,090 B2 | 8/2007 | Goetz |
| 7,260,436 B2 | 8/2007 | Kilgore et al. |
| 7,266,412 B2 | 9/2007 | Stypulkowski |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,333,857 B2 | 2/2008 | Campbell |
| 7,337,005 B2 | 2/2008 | Kim et al. |
| 7,346,398 B2 | 3/2008 | Gross et al. |
| 7,349,743 B2 | 3/2008 | Tadlock |
| 7,359,751 B1 | 4/2008 | Erickson et al. |
| 7,363,076 B2 | 4/2008 | Yun et al. |
| 7,373,204 B2 | 5/2008 | Gelfand et al. |
| 7,389,145 B2 | 6/2008 | Kilgore et al. |
| 7,393,351 B2 | 7/2008 | Woloszko et al. |
| 7,463,927 B1 | 12/2008 | Chaouat |
| 7,493,172 B2 | 2/2009 | Whitehurst et al. |
| 7,502,652 B2 | 3/2009 | Gaunt et al. |
| 7,571,007 B2 | 8/2009 | Erickson et al. |
| 7,580,753 B2 | 8/2009 | Kim et al. |
| 7,599,737 B2 | 10/2009 | Yomtov et al. |
| 7,634,317 B2 | 12/2009 | Ben-David et al. |
| 7,676,269 B2 | 3/2010 | Yun et al. |
| 7,689,276 B2 | 3/2010 | Dobak |
| 7,689,289 B2 | 3/2010 | King |
| 7,734,340 B2 | 6/2010 | De Ridder |
| 7,742,810 B2 | 6/2010 | Moffitt et al. |
| 7,761,170 B2 | 7/2010 | Kaplan et al. |
| 7,778,704 B2 | 8/2010 | Rezai |
| 7,813,803 B2 | 10/2010 | Heruth et al. |
| 7,826,901 B2 | 11/2010 | Lee et al. |
| 7,848,818 B2 | 12/2010 | Barolat et al. |
| 7,860,570 B2 | 12/2010 | Whitehurst et al. |
| 7,877,136 B1 | 1/2011 | Moffitt et al. |
| 7,890,176 B2 | 2/2011 | Jaax et al. |
| 7,933,654 B2 | 4/2011 | Merfeld et al. |
| 7,937,145 B2 | 5/2011 | Dobak |
| 8,000,794 B2 | 8/2011 | Lozano |
| 8,010,198 B2 | 8/2011 | Libbus et al. |
| 8,027,718 B2 | 9/2011 | Spinner et al. |
| 8,046,075 B2 | 10/2011 | Rezai |
| 8,060,208 B2 | 11/2011 | Kilgore et al. |
| 8,082,039 B2 | 12/2011 | Kim et al. |
| 8,170,675 B2 * | 5/2012 | Alataris et al. ............ 607/46 |
| 8,209,021 B2 * | 6/2012 | Alataris et al. ............ 607/46 |
| 8,209,028 B2 | 6/2012 | Skelton et al. |
| 8,224,453 B2 | 7/2012 | De Ridder |
| 8,224,459 B1 | 7/2012 | Pianca et al. |
| 8,280,515 B2 | 10/2012 | Greenspan |
| 8,355,792 B2 * | 1/2013 | Alataris et al. ............ 607/46 |
| 8,359,102 B2 * | 1/2013 | Alataris et al. ............ 607/46 |
| 8,359,103 B2 * | 1/2013 | Alataris et al. ............ 607/46 |
| 8,396,559 B2 * | 3/2013 | Alataris et al. ............ 607/46 |
| 8,423,147 B2 * | 4/2013 | Alataris et al. ............ 607/46 |
| 8,428,748 B2 * | 4/2013 | Alataris et al. ............ 607/117 |
| 8,612,018 B2 | 12/2013 | Gillbe |
| 8,825,166 B2 | 9/2014 | John |
| 8,886,326 B2 | 11/2014 | Alataris et al. |
| 8,886,328 B2 | 11/2014 | Alataris et al. |
| 8,892,209 B2 | 11/2014 | Alataris et al. |
| 2002/0055779 A1 | 5/2002 | Andrews |
| 2002/0128700 A1 | 9/2002 | Cross |
| 2003/0100931 A1 | 5/2003 | Mullett |
| 2003/0120323 A1 | 6/2003 | Meadows et al. |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0073273 A1 | 4/2004 | Gluckman et al. |
| 2004/0093093 A1 | 5/2004 | Andrews |
| 2004/0162590 A1 | 8/2004 | Whitehurst et al. |
| 2004/0167584 A1 | 8/2004 | Carroll et al. |

(56) References Cited

U.S. PATENT DOCUMENTS

| | | |
|---|---|---|
| 2004/0193228 A1 | 9/2004 | Gerber |
| 2004/0210270 A1 | 10/2004 | Erickson |
| 2004/0210271 A1 | 10/2004 | Campen et al. |
| 2005/0033381 A1 | 2/2005 | Carter et al. |
| 2005/0038489 A1 | 2/2005 | Grill |
| 2005/0060001 A1 | 3/2005 | Singhal et al. |
| 2005/0070982 A1 | 3/2005 | Heruth et al. |
| 2005/0113877 A1 | 5/2005 | Spinelli et al. |
| 2005/0113878 A1 | 5/2005 | Gerber |
| 2005/0113882 A1 | 5/2005 | Cameron et al. |
| 2005/0119713 A1* | 6/2005 | Whitehurst et al. ............. 607/46 |
| 2005/0143789 A1 | 6/2005 | Whitehurst et al. |
| 2005/0149148 A1 | 7/2005 | King |
| 2005/0153885 A1 | 7/2005 | Yun et al. |
| 2005/0154435 A1 | 7/2005 | Stern et al. |
| 2005/0245978 A1 | 11/2005 | Varrichio et al. |
| 2005/0246006 A1 | 11/2005 | Daniels |
| 2005/0267545 A1 | 12/2005 | Cory |
| 2005/0278000 A1 | 12/2005 | Strother et al. |
| 2006/0004422 A1 | 1/2006 | De Ridder |
| 2006/0009820 A1* | 1/2006 | Royle ............................. 607/74 |
| 2006/0015153 A1 | 1/2006 | Gliner et al. |
| 2006/0030895 A1 | 2/2006 | Simon et al. |
| 2006/0041285 A1 | 2/2006 | Johnson |
| 2006/0074456 A1 | 4/2006 | Pyles et al. |
| 2006/0079937 A1 | 4/2006 | King et al. |
| 2006/0095088 A1 | 5/2006 | De Ridder |
| 2006/0100671 A1 | 5/2006 | Ridder |
| 2006/0149337 A1 | 7/2006 | John |
| 2006/0161219 A1 | 7/2006 | Mock et al. |
| 2006/0161235 A1 | 7/2006 | King |
| 2006/0167525 A1 | 7/2006 | King |
| 2006/0168805 A1 | 8/2006 | Hegland et al. |
| 2006/0190048 A1 | 8/2006 | Gerber |
| 2006/0224187 A1 | 10/2006 | Bradley et al. |
| 2006/0229687 A1 | 10/2006 | Goetz et al. |
| 2006/0253174 A1 | 11/2006 | King |
| 2006/0253182 A1 | 11/2006 | King |
| 2007/0021803 A1 | 1/2007 | Deem et al. |
| 2007/0032827 A1 | 2/2007 | Katims |
| 2007/0039625 A1 | 2/2007 | Heruth et al. |
| 2007/0049991 A1 | 3/2007 | Klostermann et al. |
| 2007/0060954 A1* | 3/2007 | Cameron et al. .................. 607/2 |
| 2007/0066997 A1 | 3/2007 | He et al. |
| 2007/0073353 A1 | 3/2007 | Rooney et al. |
| 2007/0073354 A1* | 3/2007 | Knudson et al. ................ 607/45 |
| 2007/0073357 A1 | 3/2007 | Rooney et al. |
| 2007/0083240 A1 | 4/2007 | Peterson et al. |
| 2007/0106337 A1 | 5/2007 | Errico et al. |
| 2007/0150029 A1 | 6/2007 | Bourget et al. |
| 2007/0150034 A1 | 6/2007 | Rooney et al. |
| 2007/0156183 A1 | 7/2007 | Rhodes |
| 2007/0167992 A1 | 7/2007 | Carley |
| 2007/0179559 A1 | 8/2007 | Giftakis et al. |
| 2007/0179579 A1* | 8/2007 | Feler et al. .................... 607/117 |
| 2007/0208394 A1 | 9/2007 | King et al. |
| 2007/0239226 A1 | 10/2007 | Overstreet |
| 2007/0244522 A1 | 10/2007 | Overstreet |
| 2007/0255118 A1 | 11/2007 | Miesel et al. |
| 2007/0299482 A1 | 12/2007 | Littlewood et al. |
| 2008/0033511 A1 | 2/2008 | Dobak |
| 2008/0039904 A1 | 2/2008 | Bulkes et al. |
| 2008/0051851 A1 | 2/2008 | Lin |
| 2008/0097539 A1 | 4/2008 | Belalcazar |
| 2008/0103570 A1 | 5/2008 | Gerber |
| 2008/0154329 A1 | 6/2008 | Pyles et al. |
| 2008/0167697 A1 | 7/2008 | Johnson |
| 2008/0183259 A1 | 7/2008 | Bly et al. |
| 2008/0234791 A1 | 9/2008 | Arle et al. |
| 2008/0269854 A1 | 10/2008 | Hegland et al. |
| 2008/0281381 A1 | 11/2008 | Gerber et al. |
| 2009/0024187 A1 | 1/2009 | Erickson et al. |
| 2009/0036945 A1 | 2/2009 | Chancellor et al. |
| 2009/0054962 A1 | 2/2009 | Lefler et al. |
| 2009/0069803 A1 | 3/2009 | Starkebaum |
| 2009/0112282 A1 | 4/2009 | Kast et al. |
| 2009/0125079 A1 | 5/2009 | Armstrong et al. |
| 2009/0132010 A1 | 5/2009 | Kronberg |
| 2009/0132016 A1 | 5/2009 | Putz |
| 2009/0157141 A1 | 6/2009 | Chiao et al. |
| 2009/0157149 A1 | 6/2009 | Wahlgren et al. |
| 2009/0198306 A1 | 8/2009 | Goetz et al. |
| 2009/0204173 A1* | 8/2009 | Fang et al. ...................... 607/46 |
| 2009/0204192 A1 | 8/2009 | Carlton et al. |
| 2009/0281595 A1 | 11/2009 | King et al. |
| 2009/0287274 A1 | 11/2009 | De Ridder |
| 2009/0326611 A1 | 12/2009 | Gillbe |
| 2010/0010567 A1 | 1/2010 | Deem et al. |
| 2010/0016929 A1 | 1/2010 | Prochazka |
| 2010/0036454 A1 | 2/2010 | Bennett et al. |
| 2010/0042193 A1 | 2/2010 | Slavin |
| 2010/0057178 A1 | 3/2010 | Simon |
| 2010/0094375 A1 | 4/2010 | Donders et al. |
| 2010/0125313 A1 | 5/2010 | Lee et al. |
| 2010/0137938 A1 | 6/2010 | Kishawi et al. |
| 2010/0179562 A1 | 7/2010 | Linker et al. |
| 2010/0191307 A1 | 7/2010 | Fang et al. |
| 2010/0211135 A1 | 8/2010 | Caparso et al. |
| 2010/0241190 A1 | 9/2010 | Kilgore et al. |
| 2010/0249875 A1 | 9/2010 | Kishawi et al. |
| 2010/0256696 A1 | 10/2010 | Schleicher et al. |
| 2010/0274312 A1 | 10/2010 | Alataris et al. |
| 2010/0274314 A1* | 10/2010 | Alataris et al. .................. 607/46 |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre et al. |
| 2010/0324630 A1 | 12/2010 | Lee et al. |
| 2010/0331916 A1 | 12/2010 | Parramon et al. |
| 2011/0009919 A1 | 1/2011 | Carbunaru et al. |
| 2011/0009923 A1 | 1/2011 | Lee |
| 2011/0009927 A1 | 1/2011 | Parker et al. |
| 2011/0022114 A1 | 1/2011 | Navarro |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0016437 A1 | 1/2012 | Alataris et al. |
| 2012/0016438 A1 | 1/2012 | Alataris et al. |
| 2012/0016439 A1 | 1/2012 | Alataris et al. |
| 2012/0089200 A1 | 4/2012 | Ranu et al. |
| 2012/0158093 A1* | 6/2012 | Alataris et al. .................. 607/46 |
| 2012/0172946 A1 | 7/2012 | Alataris et al. |
| 2012/0203304 A1 | 8/2012 | Alataris et al. |
| 2012/0209349 A1 | 8/2012 | Alataris et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0041425 A1 | 2/2013 | Fang et al. |
| 2013/0096643 A1 | 4/2013 | Fang et al. |
| 2013/0096644 A1 | 4/2013 | Fang et al. |
| 2013/0110196 A1 | 5/2013 | Alataris et al. |
| 2013/0123879 A1 | 5/2013 | Alataris et al. |
| 2013/0204173 A1 | 8/2013 | Kelly et al. |
| 2013/0204320 A1 | 8/2013 | Alataris et al. |
| 2013/0204321 A1 | 8/2013 | Alataris et al. |
| 2013/0204322 A1 | 8/2013 | Alataris et al. |
| 2013/0204323 A1 | 8/2013 | Thacker et al. |
| 2013/0204338 A1 | 8/2013 | Alataris et al. |
| 2013/0211487 A1 | 8/2013 | Fang et al. |
| 2014/0031896 A1 | 1/2014 | Alataris et al. |
| 2014/0142656 A1 | 5/2014 | Alataris et al. |
| 2014/0142657 A1 | 5/2014 | Alataris et al. |
| 2014/0142658 A1 | 5/2014 | Alataris et al. |
| 2014/0142659 A1 | 5/2014 | Alataris et al. |
| 2014/0142673 A1 | 5/2014 | Alataris et al. |
| 2014/0343622 A1 | 11/2014 | Alataris et al. |
| 2014/0379044 A1 | 12/2014 | Walker et al. |
| 2015/0018896 A1 | 1/2015 | Alataris et al. |
| 2015/0032182 A1 | 1/2015 | Alataris et al. |

(56) References Cited

U.S. PATENT DOCUMENTS

| | | |
|---|---|---|
| 2015/0032183 A1 | 1/2015 | Alataris et al. |
| 2015/0039049 A1 | 2/2015 | Alataris et al. |
| 2015/0039050 A1 | 2/2015 | Alataris et al. |
| 2015/0045853 A1 | 2/2015 | Alataris et al. |
| 2015/0045854 A1 | 2/2015 | Alataris et al. |
| 2015/0051664 A1 | 2/2015 | Alataris et al. |

FOREIGN PATENT DOCUMENTS

| | | | |
|---|---|---|---|
| EP | 2243511 | A2 | 10/2010 |
| EP | 2630984 | A1 | 8/2013 |
| GB | 2449546 | A | 11/2008 |
| JP | 2002200179 | A | 7/2002 |
| JP | 2007528774 | A | 10/2007 |
| SU | 1512625 | A1 | 10/1989 |
| SU | 1690727 | A1 | 11/1991 |
| WO | WO-02065896 | A2 | 8/2002 |
| WO | WO-02092165 | A1 | 11/2002 |
| WO | WO-03015863 | A2 | 2/2003 |
| WO | WO-2004007018 | A1 | 1/2004 |
| WO | WO-2005115532 | A2 | 12/2005 |
| WO | WO-2006057734 | A1 | 6/2006 |
| WO | WO-2006084635 | A2 | 8/2006 |
| WO | WO-2007035925 | A2 | 3/2007 |
| WO | WO-2007082382 | A1 | 7/2007 |
| WO | WO-2007103324 | A1 | 9/2007 |
| WO | WO-2007117232 | A1 | 10/2007 |
| WO | WO-2008039982 | A2 | 4/2008 |
| WO | WO-2008045434 | A2 | 4/2008 |
| WO | WO-2008106174 | A1 | 9/2008 |
| WO | WO-2008121891 | A1 | 10/2008 |
| WO | WO-2008142402 | A1 | 11/2008 |
| WO | WO-2008153726 | A2 | 12/2008 |
| WO | WO-2009018518 | A1 | 2/2009 |
| WO | WO-2009061813 | A1 | 5/2009 |
| WO | WO-2009129329 | A1 | 10/2009 |
| WO | WO-2011014570 | A1 | 2/2011 |

OTHER PUBLICATIONS

U.S. Appl. No. 13/620,235, filed Sep. 14, 2012, Alataris.
U.S. Appl. No. 13/728,965, filed Dec. 27, 2012, Alataris.
Barolat et al., "Multifactorial Analysis of Epidural Spinal Cord Stimulation," Sterotactic and Functional Neurosurgery, 1991; 56: 77-103.
Bhadra et al., "High Frequency electrical conduction block of the pudendal nerve," Journal of Neural Engineering—Institute of Physics Publishing, 2006, 8 pages.
Bhadra MD, Niloy et al., "High-Frequency Electrical Conduction Block of Mammalian Peripheral Motor Nerve," Muscle and Nerve, Dec. 2005, 9 pages.
Boger et al., "Bladder Voiding by Combined High Frequency Electrical Pudendal Nerve Block and Sacral Root Stimulation," Neurourology and Urodynamics, 27, 2008, 5 pages.
Bowman and McNeal, Response of Single Alpha Motoneurons to High-Frequency Pulse Trains, Appl. Neurophysiol. 49, p. 121-138, 1986, 10 pages.
Burton, Charles, "Dorsal Column Stimulation: Optimization of Application," Surgical Neurology, vol. 4, No. 1, Jul. 1975, 10 pages.
DeRidder et al., "Are Parenthesis necessary for pain suppression in SCS—Burst Stimulation," Brain, Brain Research Center Antwerp of Innovative and Interdisciplinary Neuromodulation, 2010, 27 pages.
DeRidder et al., "Burst Spinal Cord Stimulation: Toward Paresthesia-Free Pain Suppression," www.neurosurgery-online.com, vol. 66, Nos. 5, May 2010, 5 pages.
Grill, Warren et al., "Stimulus Waveforms for Selective Neural Stimulation," IEEE Engineering in Medicine and Biology, Jul./Aug. 1995, pp. 375-385.
Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.
Hopp et al., "Effect of anodal blockade of myelinated fibers on vagal c-fiber afferents," American Journal Physiological Society, Nov. 1980; 239(5), 9 pages.
Hoppenstein, Reuben, "Electrical Stimulation of the Ventral and Dorsal Columns of the Spinal Cord for Relief of Chronic Intractable Pain: Preliminary Report," Surgical Neurology, vol. 4, No. 1, Jul. 1975, 9 pages.
Huxely et al., "Excitation and Conduction in Nerve: Quantitative Analysis," Science, Sep. 11, 1964; 145: 1154-9.
International Search Report and Written Opinion for International Patent Application No. PCT/US12/54324, Applicant: James R. Thacker, mailed Nov. 16, 2012, 11 pages.
Jang et al., "Analysis of Failed Spinal Cord Stimulation Trails in the Treatment of Intractable Chronic Pain," J. Korean Neurosurg Soc 43, 2008, 5 pages.
Kilgore et al. "Nerve Conduction Block Utilizing High-Frequency Alternating Current" Medical & Biology Engineering and Computing, 2004, vol. 24, pp. 394-406.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Linderoth et al., "Mechanisms of Spinal Cord Stimulation in Painful Syndromes: Role of Animal Models," Pain Medicine, vol. 7, No. S1, 2006, 13 pages.
Linderoth et al., "Physiology of Spinal Cord Stimulation: Review and Update," Neuromodulation, vol. 2, No. 3, 1999, 15 pages.
Mediati, R.D., , "Mechanisms of Spinal Cord Stimulation," Florence, Oct. 2, 2002, 31 pages.
Melzack, Ronald et al., "Pain Mechanisms: A New Theory," Science, vol. 150, No. 3699, Nov. 19, 1965, 9 pages.
Muller and Hunsperger, "Helvetica Physiologica Acta—Reversible Blockierung der Erregungsleitung im Nerven durch Mittelfrequenz-Daverstrom," Schwabe & Co. Basel, vol. 25, Fasc. 1, 1967, 4 pages.
North et al., "Failed Back Surgery Syndrome: 5-year Follow-Up after Spinal Cord Stimulator Implantation," Neurosurgery, Offical Journal of the Congress of Neurological Surgeons, vol. 28, No. 5, May 1991, 9 pages.
North et al., "Spinal Cord Stimulation for Axial Low Back Pain," SPINE, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
Oakley, John C., "Spinal Cord Stimulation Mechanisms of Action," SPINE vol. 27, No. 22, copyright 2002, 10 pages.
Shealy MD, C. Norman et al., "Electrical Inhibition of Pain by Stimulation of the Dorsal Columns: Preliminary Clinical Report," Anesthesia and Analgesia . . . Current Researches, vol. 446, No. 4, Jul.-Aug. 1967, 3 pages.
Simpson, BA, "Spinal Cord Stimulation in 60 cases of Intractable Pain." Journal of Neurology, Neurosurgery and Psychiatry, 1991; 54 pp. 196-199.
Simpson, BA, "Spinal Cord Stimulation." British Journal of Neurosurgery, Feb. 11, 1997 (1), 5-11, 7 pages.
Solomonow et al., "Control of Muscle Contractile Force through Indirect High-Frequency Stimulation," AM Journal of Physical Medicine, 1983, vol. 62, No. 3, pp. 71-82.
Tanner, J.A., "Reversible blocking of nerve conduction by alternating-current excitation," Nature, Aug. 18, 1962; 195: 712-3.
Urban et al., "Percutaneous epidural stimulation of the spinal cord for relief of pain—Long Term Results," Journal of Neurosurgery, vol. 48, Mar. 1978, 7 pages.
Van Den Honert et al. "Generation of Unidirectionally Propagated Action Potentials Nerve by Brief Stimuli" Science, vol. 26, pp. 1311-1312.
Van Den Honert, Mortimer JT, "A Technique for Collision Block of Peripheral Nerve: Frequency Dependence," MP-11 IEEE Trans. Biomed, Eng. 28: 379-382, 1981.
Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.

(56) References Cited

OTHER PUBLICATIONS

Woo MY, Campbell B. "Asynchronous Firing and Block of Peripheral Nerve Conduction by 20KC Alternating Current," Los Angeles Neuro Society, Jun. 1964; 87-94, 5 pages.
Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.
U.S. Appl. No. 13/831,381, filed Mar. 14, 2013, Thacker et al.
U.S. Appl. No. 13/831,300, filed Mar. 14, 2013, Thacker et al.
U.S. Appl. No. 13/831,539, filed Mar. 14, 2013, Thacker et al.
Alo et al., "New Trends in Neuromodulation for the Management of Neuropathic Pain," Neurosurgery, vol. 50, No. 4, Apr. 2002, 15 pages.
Cuellar et al., "Effect of High Frequency Alternating Current on Spinal Afferent Nociceptive Transmission," Neuromodulation: Technology at the Neural Interface, 2012, 10 pages.
Kilgore et al. "Reversible Nerve Conduction Block Using Kilohertz Frequency Alternating Current," Neuromodulation Technology at the Neural Interface, International Neuromodulation Society, 2013, 13 pages.
Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.
Tiede et al., "Novel Spinal Cord Stimulation Parameters ; in Patients with Predominate Back Pain," Neuromodulation:; Technology at the Neural Interface, 2013, 6 pages.
Van Butyen et al., "High Frequency Spinal Cord Stimulation for the ; Treatment of Chronic Back Pain Patients: Results of a Prospective ; Multicenter European Clinical Study," Neuromodulation Technology at the ; Neural Interface, International Neuromodulation Society, 2012, 8 pages.
Bahdra et al., Stimulation of High-Frequency Sinusoidal Electrical Block of Mammalian Myelinated Axons, J Comput Neurosco, 22:313-326, 2007.
Amendment in Response to Ex Parte Office Action for U.S. Appl. No. 13/446,970, First Named Inventor: Konstantinos Alataris, Mailed: Nov. 28, 2012, 14 pages.
Amendment in Response to Non-Final Office Action for U.S. Appl. No. 13/245,450, First Named Inventor: Konstantinos Alataris, filed: Feb. 7, 2012, 15 pages.
Amendment in Response to Non-Final Office Action for U.S. Appl. No. 12/765,747, First Named Inventor: Konstantinos Alataris, Mailed: Jan. 24, 2014, 21 pages.
Applicant-Initiated Interview Summary for U.S. Appl. No. 13/245,450, First Named Inventor: Konstantinos Alataris, Mailed: Feb. 1, 2012, 2 pages.
Application Data Sheet for U.S. Appl. No. 13/446,970 (USP8,359,102), First Named Inventor: Konstantinos Alataris, Filed: Apr. 13, 2012, 6 pages.
Barolat et al., "Surgical Management of Pain—Spinal Cord Stimulation: Equipment and Implantation Techniques," Chapter 41, Thieme Medical Publishers, New York, 2002, 11 pages.
Crosby et al., "Stimulation Parameters Define the Effectiveness of Burst Spinal Cord Stimulation in a Rat Model of Neuropathic Pain," Neuromodulation Technology at the Neural Interface, International Neurmodulation Society, 2014, 8 pages.
Declaration of Cameron C. McIntyre, Ph.D., May 6, 2015, 88 pages.
Declaration of Cameron C. McIntyre, Ph.D., May 6, 2015, 57 pages.
Declaration of M. Jason D. Rahn, Jan. 7, 2015, 7 pages.
Doug Atkins of Medtronic Neurological, "Medtronic Neurostimulation Leads, 510(k) Summary," Submission Prepared: Feb. 27, 2004, 6 pages.
Ex Parte Office Action for U.S. Appl. No. 13/446,970, First Inventor Named: Konstantinos Alataris, Mailed: Oct. 15, 2012, 9 pages.
First Preliminary Amendment for U.S. Appl. No. 13/446,970, First Named Inventor: Konstantinos Alataris, Mailed: May 18, 2012, 7 pages.
Guo et al., "Design and Implement of a Mini-Instrument for Rehabilitation with Transcutaneous Electrical Nerve Stimulation," School of Medical Instrument and Food Engineering, University of Shanghai for Science and Technology, Shanghai China, Mar. 31, 2007, 5 pages.
Medtronic—Neurological Division, QuadPlus, Model 3888, Lead Kit for Spinal Cord Stimulation (SCS) Implant Manual, 1996, 33 pages.
Medtronic—Neurological Division, Resume II, Model 3587A, Lead Kit for Spinal Cord Stimulation (SCS) and Peripheral Nerve Stimulation (PNS), Implant Manual, 1996, 32 pages.
Medtronic—Neurological Division, Resume TL, Model 3986, Lead Kit for Spinal Cord Stimulation (SCS) and Peripheral Nerve Stimulation (PNS), Implant Manual, 1996, 27 pages.
Medtronic—Neurostimulation Systems: Expanding the Array of Pain Control Solutions, 1999, 6 pages.
Medtronic commercial leaflet entitled: 'Surgical Lead Comparison," 1999, 4 pages.
Medtronic, Pain Therapy Product Guide, Dec. 2008, 31 pages.
Medtronic, Pisces Quad 3487A, Pisces Quad Compact model 3887, Pisces Quad Plus 3888 Lead Kit, Implant Manual, 2008, 16 pages.
Medtronic: Spinal Cord Stimulation Systems, 2013, 4 pages.
Merriam Webster's Collegiate Dictionary, Tenth Edition, definition of "Implantable," 1995, 3 pages.
Munglani, Rajesh, "The Longer Term Effect of Pulsed Radiofrequency for Neuropathic Pain," Pain 80, 1999, 3 pages.
Non-Final Office Action for U.S. Appl. No. 12/765,747, First Named Inventor: Konstantinos Alataris, Mailed: Jul. 25, 2013, 7 pages.
Non-Final Office Acton for U.S. Appl. No. 13/245,450, First Named Inventor: Konstantinos Alataris, Mailed Nov. 18, 2011, 11 pages.
Notice of Allowance for U.S. Appl. No. 13/245,450, First Named Inventor: Konstantinos Alataris, Mailed: Mar. 14, 2012, 8 pages.
Notice of Opposition to a European Patent, Argument and Facts for European Patent No. 2630984, Proprietor of the Patent: Nevro Corporation; Opponent: Medtronic, Mar. 17, 2015, 17 pages.
Notice of Opposition to a European Patent, Argument and Facts, and Annex for European Patent No. 2630984, Proprietor of the Patent: Nevro Corporation; Opponent: Boston Scientific Neuromodulation Corporation, Mar. 17, 2015, 21 pages.
Notice of Opposition to a European Patent, Argument and Facts, and Annex for European Patent No. 2421600, Proprietor of the Patent: Nevro Corporation; Opponent: Boston Scientific Neuromodulation Corporation, Dec. 4, 2014, 22 pages.
Notice of Opposition to a European Patent, Argument and Facts, for European Patent No. 2243510, Proprietor of the Patent: Nevro Corporation, Opponent: Medtronic, Jan. 8, 2015, 22 pages.
Notice of Opposition to a European Patent, Argument and Facts, and Annex for European Patent No. 2243510, Proprietor of the Patent: Nevro Corporation; Opponent: Boston Scientific Neuromodulation Corporation, Jan. 8, 2015, 28 pages.
Petition for Inter Partes Review of Claims 1, 2, 11-15, 17-23, 25 and 26 for U.S. Pat. No. 8,359,102, Petitioner: Boston Scientific Neuromodulation Corporation, Patent Owner: Nevro Corporation, Attorney Ref: 1014.0248AB2, May 14, 2015, 45 pages.
Petition for Inter Partes Review of Claims 1, 2, 11-15, 17-23, 25 and 26 for U.S. Pat. No. 8,359,102, Petitioner: Boston Scientific Neuromodulation Corporation, Patent Owner: Nevro Corporation, May 14, 2015, 67 pages.
Resume of Jason D. Rahn, Jan. 7, 2015, 2 pages.
Sluijter et al., "The Effects of Pulsed Radiofrequency Fields Applied to the Dorsal Root Ganglion—A Preliminary Report," The Pain Clinic, vol. 11, No. 2, 1998, 12 pages.
St. Jude Medical, "Individualized Therapy through Diverse Lead Options," 2008, 6 pages.
Tesfaye et al., "Electrical Spinal Cord Stimulation for Painful Diabetic Peripheral Neuropathy," The Lancet, vol. 348, Dec. 21-28, 1996, 4 pages.
Tollison et al., "Practical Pain Management; Neurostimulation Techniques," Chapter 12, Lippincott Williams and Wilkins, Third Edition, 2002, 13 pages.
Van Havenbergh et al., "Spinal Cord Stimulation for the Treatment of Chronic Back Pain Patients: 500-Hz vs. 1000-Hz Burst Stimulation," Neuromodulation: Technology at the Neural Interface, International Neurmodulation Society, 2014, 4 pages.
"The Need for Mechanism-Based Medicine in Neuromodulation," Neuromodulation: Technology at the Neural Interface, 2012, 7 pages.

(56) References Cited

OTHER PUBLICATIONS

Al-Kaisy et al., "Sustained Effectiveness of 10kHz High-Frequency Spinal Cord Stimulation for Patients with Chronic, Low Back Pain: 24-month Results of Prospective Multicenter Study," Pain Medicine, 2014, 8 pages.

Applicant-Initiated Interview Summary for U.S. Appl. No. 13/725,770, First Named Inventor: Konstantinos Alataris, Mailed: Apr. 5, 2013, 3 pages.

Applicant-Initiated Interview Summary for U.S. Appl. No. 12/765,747, First Named Inventor: Konstantinos Alataris, Mailed: Sep. 11, 2013, 3 pages.

Boston Scientific "Precision™ Spinal Cord Stimulator System Clinician Manual—Directions for Use," 2015, 74 pages.

Boston Scientific, News Release: "New Data Presented at NANS 2014 Demonstrate Long-Term, Low Back Pain Relief with Boston Scientific Precision Spectra™ Spinal Cord Stimulator System," Dec. 12, 2014, 8 pages.

ClinicalTrials.gov, "Safety and Effectiveness Study of the Precision SCS System Adapted for High-Rate Spinal Cord Stimulation (ACCELERATE)," https://clinicaltrials.gov/ct2/show/NCT02093793?term=boston+scientific&recr=Open&cond=%22Pain%22&rank=3, Feb. 2015, 3 pages.

Dorland's Illustrated Medical Dictionary, Twenty-sixth Edition, "Paresthesia," 1981, 4 pages.

J.P. Morgan North America Equity Research, "Nevro—Let the Launch Begin: Senza Approved, Raising PT to $54," www.jpmorganmarkets.com, May 10, 2015, 8 pages.

J.P. Morgan North America Equity Research, "Nevro—Welcome to the Future of Spinal Cord Stimulation Initiating at OW with $34 Price Target," www.jpmorganmarkets.com, Dec. 1, 2014, 39 pages.

Jain et al., Abstract— "Accelerate: A Prospective Multicenter Trial Evaluating the Use of High-Rate Spinal Cord Stimulation in the Management of Chronic Intractable Pain," The American Academy of Pain Medicine, 2015, 1 page.

JMP Securities, "Nevro Corp. (NVRO) Initiating Coverage on Nevro Corp. with a Market Outperform Rating—Investment Highlights," Dec. 1, 2014, 42 pages.

Kapural et al., "Novel 10-Khz High Frequency Therapy (HF10 Therapy) is Superior to Traditional Low-Frequency Spinal Cord Stimulation for Treatment of Chronic Back and Leg Pain," Anesthesiology The Journal of American Society of Anesthesiologists, Inc., 2015, 11 pages.

Kuechmann et al., Abstract #853: "Could Automatic Position Adaptive Stimulation Be Useful in Spinal Cord Stimulation?" Medtronic, Inc., Minneapolis, MN, European Journal of Pain 13, 2009, 1 page.

Kumar et al., "The Effects of Spinal Cord Stimulation in Neuropathic Pain Are Sustained: A 24-month Follow-Up of the Prospective Randomized Controlled Multicenter Trial of the Effectiveness of Spinal Cord Stimulation," www.neurosurgery-online.com, vol. 63, No. 4, Oct. 2008, 9 pages.

Lempka et al., "Computational Analysis of Kilohertz Frequency Spinal Cord Stimulation for Chronic Pain Management," Anesthesiology, vol. 122, No. 6, Jun. 2015, 15 pages.

Linderoth et al., "Mechanisms of Spinal Cord Stimulation in Neuropathic and Ischemic Pain Syndromes," Neuromodulation, Chapter 25, 2009, 19 pages.

Medtronic, "Medtronic Pain Therapy—Using Neurostimulation for Chronic Pain, Information for Prescribers" 2007, 29 pages.

Morgan Stanley Research North America, "Nevro Corp—There's Something Happening Here," Dec. 15, 2014, 12 pages.

Mosby's Medical Dictionary, 8th Edition, "Paresthesia," 2009, 3 pages.

Nevro Senza Patient Manual, Jan. 16, 2015, 53 pages.

Nevro Senza Physician Implant Manual, Jan. 16, 2015, 31 pages.

Nevro, PMA Approval Letter and Referenced Summary of Safety and Effectiveness Data (SSED) May 8, 2015, 60 pages.

News Release Details, "Nevro Corp. Announces Pricing of Initial Public Offering," 2014, 1 page.

North American Neuromodulation Society—14th Annual Meeting, "Neuromodulation: Vision 2010," Dec. 2-5, 2010, 9 pages.

North American Neuromodulation Society—16th Annual Meeting, "From Innovation to Reality Syllabus," Dec. 6-9, 2012, 198 pages.

North American Neuromodulation Society—Celebrating 20 years, 18th Annual Meeting Program Book, Dec. 11-14, 2014, 28 pages.

North American Neuromodulation Society, "Today's Vision, Tomorrow's Reality—17th Annual Meeting," Dec. 5-8, 2013, 12 pages.

North American Neuromodulation, "15th Annual Meeting, Our Crystal Anniversary," Dec. 8-11, 2011, 8 pages.

Oakley et al., "A New Spinal Cord Stimulation System Effectively Relieves Chronic, Intractable Pain: A Multicenter Prospective Clinical Study," Neuromodulation: Technology at the Neural Interface, vol. 10, No. 3, 2007, 17 pages.

Oakley et al., "Spinal Cord Stimulation in Axial Low Back Pain: Solving the Dilemma," Pain Medicine, vol. 7, Number S1, 2006, 6 pages.

Patent Owner's Preliminary Response for Inter Partes Review for U.S. Pat. No. 8,359,102, Case No. IPR2015-01203, Petitioner: Boston Scientific Neuromodulation Corporation, Patent Owner: Nevro Corporation, mailed Sep. 1, 2015, 70 pages.

Patent Owner's Preliminary Response for Inter Partes Review for U.S. Pat. No. 8,359,102, Case No. IPR2015-01204, Petitioner: Boston Scientific Neuromodulation Corporation, Patent Owner: Nevro Corporation, mailed Sep. 1, 2015, 63 pages.

Prausnitz et al., "The Effects of Electric Current Applied to Skin: A Review for Transdermal Drug Delivery," Advanced Drug Delivery Reviews 18, ; 1996, 31 pages.

Science Daily, "Chronic Pain Costs U.S. up to $635 billion, study shows," www.sciencedaily.com/releases/2012/09/120911091100.htm, Sep. 11, 2012, 2 pages.

St. Jude Medical, "Eon Mini™ Rechargeable IPG," Apr. 29, 2013, 3 pages.

Stimwave, News Release: "Stimwave Receives FDA Approval for High Frequency IDE," http://stimwave.com/newsroom/latest-news, Jun. 9, 2015, 2 pages.

Wallace et al., Poster: "Accelerate: A Prospective Multicenter Trial Evaluating the Use of High-Rate Spinal Cord Stimulation in the Management of Chronic Intractable Pain," Boston Scientific Corporation, 2015, 1 page.

Webster's Third New International Dictionary of the English Language Unabridge, "Paresthesia," 1993, 3 pages.

Notice of Opposition to a European Patent, Argument and Facts, for European Patent No. 2207587, Proprietor of the Patent: Nevro Corporation; Opponent: Medtronics, Inc. Jan. 12, 2016, 22 pages.

Notice of Opposition to a European Patent, Argument and Facts, for European Patent No. 2207587, Proprietor of the Patent: Nevro Corporation; Opponent: Boston Scientific Neuromodulation Corporation, Jan. 18, 2016, 17 pages.

* cited by examiner

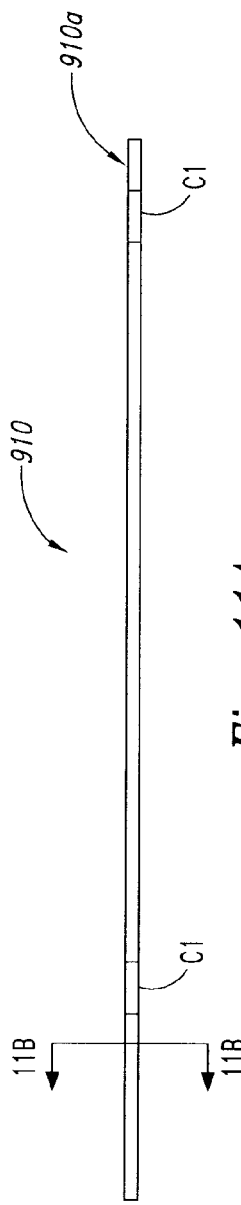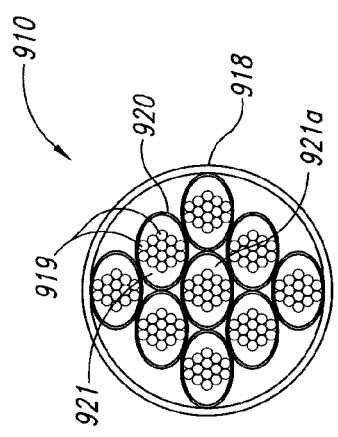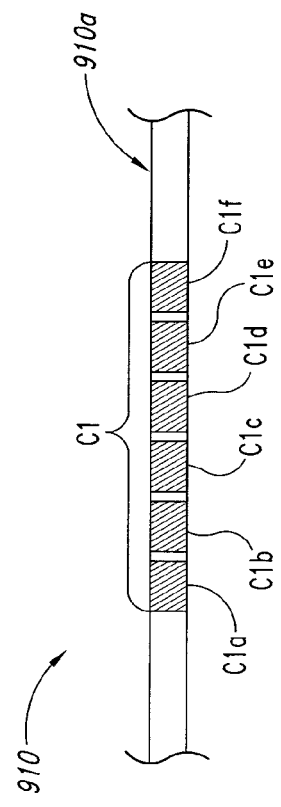
Fig. 11A
Fig. 11B
Fig. 11C

SELECTIVE HIGH FREQUENCY SPINAL CORD MODULATION FOR INHIBITING PAIN, INCLUDING CEPHALIC AND/OR TOTAL BODY PAIN WITH REDUCED SIDE EFFECTS, AND ASSOCIATED SYSTEMS AND METHODS

CROSS-REFERENCE TO RELATED APPLICATIONS

The present application is a continuation of U.S. patent application Ser. No. 13/607,617, filed on Sep. 7, 2012 which claims priority to the following U.S. Provisional Applications, both of which are incorporated herein by reference: 61/532,523, filed Sep. 8, 2011 and 61/568,135, filed Dec. 7, 2011. To the extent the foregoing applications and/or any other materials incorporated herein by reference conflict with the present disclosure, the present disclosure controls.

TECHNICAL FIELD

The present disclosure is directed generally to selective high frequency spinal cord modulation for inhibiting pain, including total body pain and/or headache pain with reduced side effects, and associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a large needle inserted into the epidural space, with or without the assistance of a stylet.

Once implanted, the pulse generator applies electrical pulses to the electrodes, which in turn modify the function of the patient's nervous system, such as by altering the patient's responsiveness to sensory stimuli and/or altering the patient's motor-circuit output. In pain treatment, the pulse generator applies electrical pulses to the electrodes, which in turn can generate sensations that mask or otherwise alter the patient's sensation of pain. For example, in many cases, patients report a tingling or paresthesia that is perceived as more pleasant and/or less uncomfortable than the underlying pain sensation. While this may be the case for many patients, many other patients may report less beneficial effects and/or results. Accordingly, there remains a need for improved techniques and systems for addressing patient pain.

BRIEF DESCRIPTION OF THE DRAWINGS

FIGS. 11A-11C are partially schematic illustrations of multifilar leads configured in accordance with several embodiments of the disclosure.

DETAILED DESCRIPTION

1.0 Introduction

The present technology is directed generally to spinal cord modulation and associated systems and methods for inhibiting pain via waveforms with high frequency elements or components (e.g., portions having high fundamental frequencies), generally with reduced or eliminated side effects. Such side effects can include unwanted motor stimulation or blocking, and/or interference with sensory functions other than the targeted pain. Several embodiments also provide simplified spinal cord modulation systems and components, and simplified procedures for the practitioner and/or the patient. Specific details of certain embodiments of the disclosure are described below with reference to methods for modulating one or more target neural populations (e.g., nerves) or sites of a patient, and associated implantable structures for providing the modulation. Although selected embodiments are described below with reference to modulating the dorsal column, dorsal horn, dorsal root, dorsal root entry zone, and/or other particular regions of the spinal column to control pain, the modulation may in some instances be directed to other neurological structures and/or target neural populations of the spinal cord and/or other neurological tissues. Some embodiments can have configurations, components or procedures different than those described in this section, and other embodiments may eliminate particular components or procedures. A person of ordinary skill in the relevant art, therefore, will understand that the disclosure may include other embodiments with additional elements, and/or may include other embodiments without several of the features shown and described below with reference to FIGS. 1A-14.

In general terms, aspects of many of the following embodiments are directed to producing a therapeutic effect that includes pain reduction in the patient. The therapeutic effect can be produced by inhibiting, suppressing, downregulating, blocking, preventing, or otherwise modulating the activity of the affected neural population. In many embodiments of the presently disclosed techniques, therapy-induced paresthesia is not a prerequisite to achieving pain reduction, unlike standard SCS techniques. It is expected that the techniques described below with reference to FIGS. 1A-14 can produce more effective, more robust, less complicated and/or otherwise more desirable results than can existing spinal cord stimulation therapies.

Figure 1A:
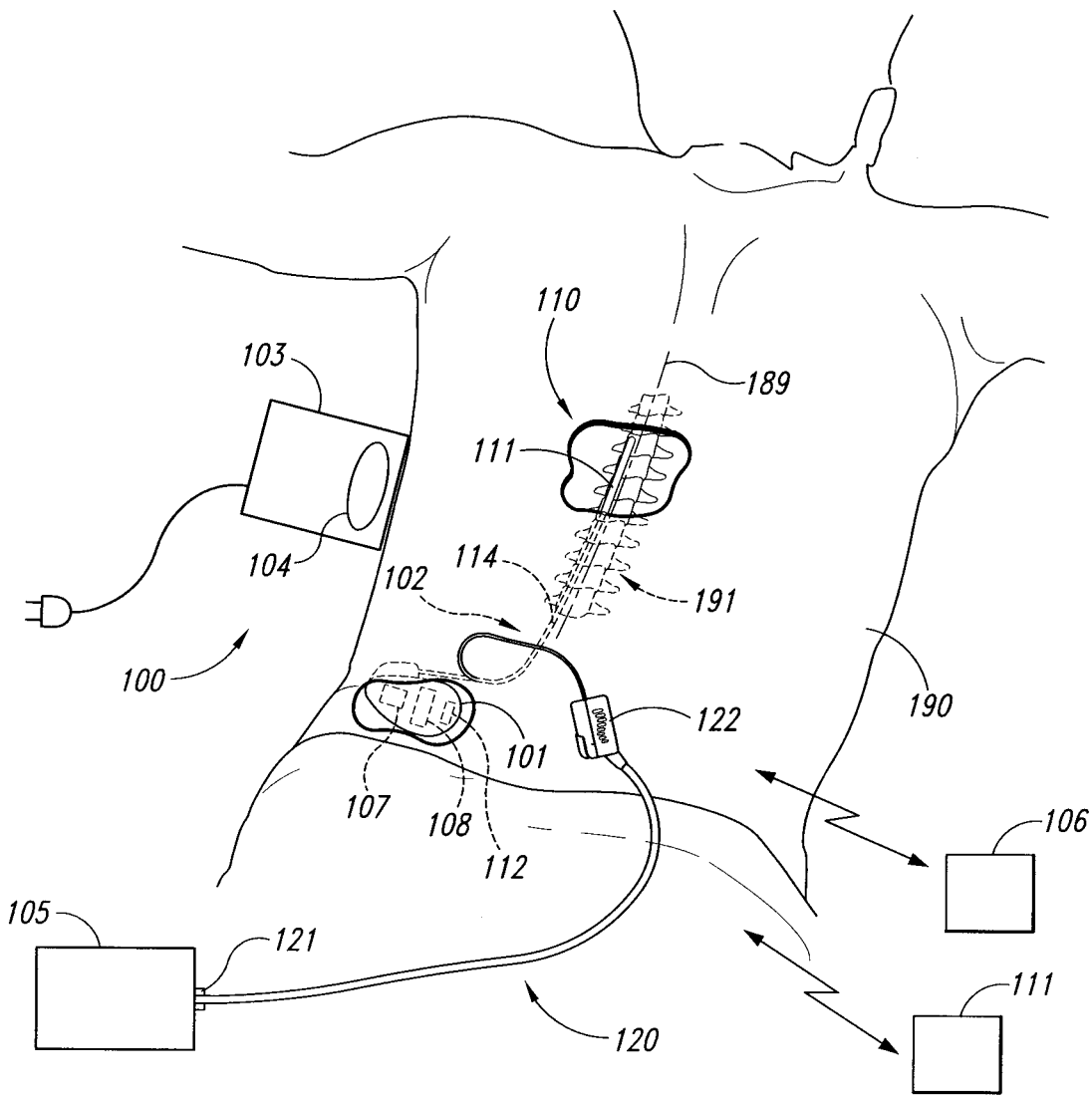
FIG. 1A is a partially schematic illustration of an implantable spinal cord modulation system positioned at the spine to deliver therapeutic signals in accordance with several embodiments of the present disclosure.

FIG. 1A schematically illustrates a representative treatment system 100 for providing relief from chronic pain and/or other conditions, arranged relative to the general anatomy of a patient's spinal cord 191. The system 100 can include a pulse generator 101, which may be implanted subcutaneously within a patient 190 and coupled to a signal delivery element 110. In a representative example, the signal delivery element 110 includes a lead or lead body 111 that carries features for delivering therapy to the patient 190 after implantation. The pulse generator 101 can be connected directly to the lead 111, or it can be coupled to the lead 111 via a communication link 102 (e.g., an extension). Accordingly, the lead 111 can include a terminal section that is releasably connected to an extension at a break 114 (shown schematically in FIG. 1A). This allows a single type of terminal section to be used with patients of different body types (e.g., different heights). As used herein, the terms lead and lead body include any of a number of suitable substrates and/or support members that carry devices for providing therapy signals to the patient 190. For example, the lead 111 can include one or more electrodes or electrical contacts that direct electrical signals into the patient's tissue, such as to provide for patient relief. In other embodiments, the signal delivery element 110 can include devices other than a lead body (e.g., a paddle) that also direct electrical signals and/or other types of signals to the patient 190.

The pulse generator 101 can transmit signals (e.g., electrical signals) to the signal delivery element 110 that up-regulate (e.g., stimulate or excite) and/or down-regulate (e.g., block or suppress) target nerves. As used herein, and unless otherwise noted, the terms "modulate" and "modulation" refer generally to signals that have either type of the foregoing effects on the target nerves. The pulse generator 101 can include a machine-readable (e.g., computer-readable) medium containing instructions for generating and transmitting suitable therapy signals. The pulse generator 101 and/or other elements of the system 100 can include one or more processors 107, memories 108 and/or input/output devices. Accordingly, the process of providing modulation signals and executing other associated functions can be performed by computer-executable instructions contained on computer-readable media, e.g., at the processor(s) 107 and/or memory(s) 108. The pulse generator 101 can include multiple portions, elements, and/or subsystems (e.g., for directing signals in accordance with multiple signal delivery parameters), housed in a single housing, as shown in FIG. 1A, or in multiple housings.

The pulse generator 101 can also receive and respond to an input signal received from one or more sources. The input signals can direct or influence the manner in which the therapy instructions are selected, executed, updated and/or otherwise performed. The input signal can be received from one or more sensors 112 (one is shown schematically in FIG. 1A for purposes of illustration) that are carried by the pulse generator 101 and/or distributed outside the pulse generator 101 (e.g., at other patient locations) while still communicating with the pulse generator 101. The sensors 112 can provide inputs that depend on or reflect patient state (e.g., patient position, patient posture and/or patient activity level), and/or inputs that are patient-independent (e.g., time). In other embodiments, inputs can be provided by the patient and/or the practitioner, as described in further detail later. Still further details are included in co-pending U.S. application Ser. No. 12/703,683, filed on Feb. 10, 2010 and incorporated herein by reference.

In some embodiments, the pulse generator 101 can obtain power to generate the therapy signals from an external power source 103. The external power source 103 can transmit power to the implanted pulse generator 101 using electromagnetic induction (e.g., RF signals). For example, the external power source 103 can include an external coil 104 that communicates with a corresponding internal coil (not shown) within the implantable pulse generator 101. The external power source 103 can be portable for ease of use.

In another embodiment, the pulse generator 101 can obtain the power to generate therapy signals from an internal power source, in addition to or in lieu of the external power source 103. For example, the implanted pulse generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

In some cases, an external programmer 105 (e.g., a trial modulator) can be coupled to the signal delivery element 110 during an initial implant procedure, prior to implanting the pulse generator 101. For example, a practitioner (e.g., a physician and/or a company representative) can use the external programmer 105 to vary the modulation parameters provided to the signal delivery element 110 in real time, and select optimal or particularly efficacious parameters. These parameters can include the position of the signal delivery element 110, as well as the characteristics of the electrical signals provided to the signal delivery element 110. In a typical process, the practitioner uses a cable assembly 120 to temporarily connect the external programmer 105 to the signal delivery device 110. The cable assembly 120 can accordingly include a first connector 121 that is releasably connected to the external programmer 105, and a second connector 122 that is releasably connected to the signal delivery element 110. Accordingly, the signal delivery element 110 can include a connection element that allows it to be connected to a signal generator either directly (if it is long enough) or indirectly (if it is not). The practitioner can test the efficacy of the signal delivery element 110 in an initial position. The practitioner can then disconnect the cable assembly 120, reposition the signal delivery element 110, and reapply the electrical modulation. This process can be performed iteratively until the practitioner obtains the desired position for the signal delivery device 110. Optionally, the practitioner may move the partially implanted signal delivery element 110 without disconnecting the cable assembly 120. Further details of suitable cable assembly methods and associated techniques are described in co-pending U.S. application Ser. No. 12/562,892, filed on Sep. 18, 2009 and incorporated herein by reference. As will be discussed in further detail later, particular aspects of the present disclosure can advantageously reduce or eliminate the foregoing iterative process.

After the position of the signal delivery element 110 and appropriate signal delivery parameters are established using the external programmer 105, the patient 190 can receive therapy via signals generated by the external programmer 105, generally for a limited period of time. In a representative application, the patient 190 receives such therapy for one week. During this time, the patient wears the cable assembly 120 and the external programmer 105 outside the body. Assuming the trial therapy is effective or shows the promise of being effective, the practitioner then replaces the external programmer 105 with the implanted pulse generator 101, and programs the pulse generator 101 with parameters selected based on the experience gained during the trial period. Optionally, the practitioner can also replace the signal delivery element 110. Once the implantable pulse generator 101 has been positioned within the patient 190, the signal delivery parameters provided by the pulse generator 101 can still be updated remotely via a wireless physician's programmer (e.g., a physician's remote) 111 and/or a wireless patient programmer 106 (e.g., a patient remote). Generally, the patient 190 has control over fewer parameters than does the practitioner. For example, the capability of the patient programmer 106 may be limited to starting and/or stopping the pulse generator 101, and/or adjusting the signal amplitude.

In any of the foregoing embodiments, the parameters in accordance with which the pulse generator 101 provides signals can be modulated during portions of the therapy regimen. For example, the frequency, amplitude, pulse width and/or signal delivery location can be modulated in accordance with a preset program, patient and/or physician inputs, and/or in a random or pseudorandom manner. Such parameter variations can be used to address a number of potential clinical situations, including changes in the patient's perception of pain, changes in the preferred target neural population, and/or patient accommodation or habituation.

Certain aspects of the foregoing systems and methods may be simplified or eliminated in particular embodiments of the present disclosure. For example, in at least some instances, the therapeutic signals delivered by the system can produce an effect that is much less sensitive to lead location and signal delivery parameters (e.g., amplitude) than are conventional stimulation systems. Accordingly, as noted above, the trial and error process (or parts of this process) for identifying a suitable lead location and associated signal delivery parameters during the lead implant procedure can be eliminated. In addition to or in lieu of this simplification, the post-lead implant trial period can be eliminated. In addition to or in lieu of the foregoing simplifications, the process of selecting signal delivery parameters and administering the signals on a long-term basis can be significantly simplified. Further aspects of these and other expected beneficial results are discussed in greater detail below.

2.0 Representative Therapy Parameters

Nevro Corporation, the assignee of the present application, has conducted a multi-site clinical study during which multiple patients were first treated with conventional spinal cord stimulation (SCS) techniques, and then with newly developed techniques that are disclosed further below. This study was followed up by a further clinical study focusing on the newly developed techniques, which confirmed and expanded on results obtained during the initial study. Multiple embodiments of the newly developed techniques, therapies and/or systems are referred to as presently disclosed techniques, therapies, and/or systems, or more generally as presently disclosed technologies.

2.1. Initial Comparison Study

Figure 1B:
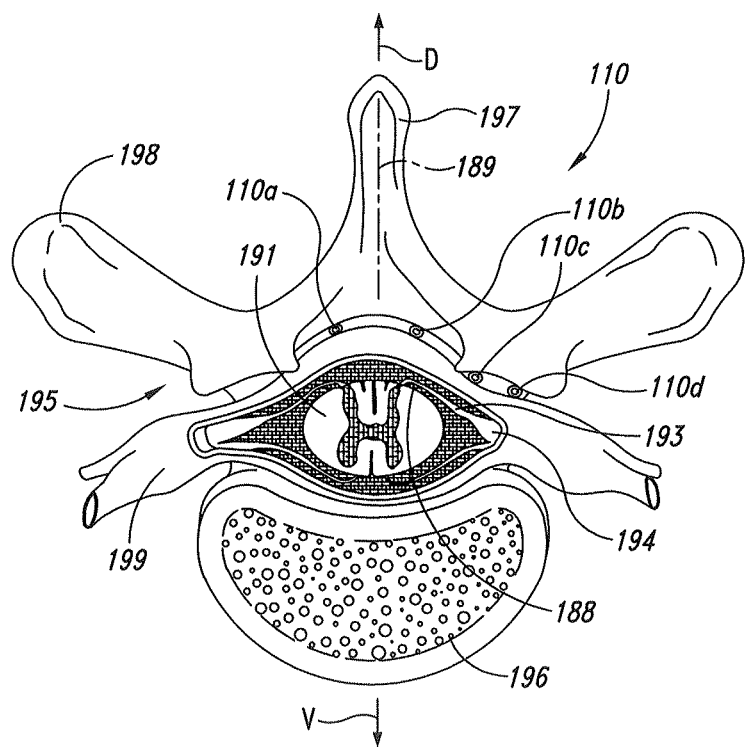
FIG. 1B is a partially schematic, cross-sectional illustration of a patient's spine, illustrating representative locations for implanted lead bodies in accordance with embodiments of the disclosure.

Prior to the initial clinical study, selected patients were identified as suffering from primary chronic low back pain (e.g., neuropathic pain, and/or nociceptive pain, and/or other types of pain, depending upon the patient), either alone or in combination with pain affecting other areas, typically the patient's leg(s). In all cases, the low back pain was dominant. During the study, the patients were outfitted with two leads, each implanted in the spinal region in a manner generally similar to that shown in FIG. 1A. One lead was implanted on one side of the spinal cord midline 189, and the other lead was implanted on the other side of the spinal cord midline 189. FIG. 1B is a cross-sectional illustration of the spinal cord 191 and an adjacent vertebra 195 (based generally on information from Crossman and Neary, "Neuroanatomy," 1995 (published by Churchill Livingstone)), along with the locations at which leads 110 were implanted in a representative patient. The spinal cord 191 is situated between a ventrally located ventral body 196 and the dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the dorsal roots 193 and dorsal root ganglia 194. The leads 110 were positioned just off the spinal cord midline 189 (e.g., about 1 mm. offset) in opposing lateral directions so that the two leads 110 were spaced apart from each other by about 2 mm.

Patients with the leads 110 located as shown in FIG. 1B initially had the leads positioned at vertebral levels T7-T8. This location is typical for standard SCS treatment of low back pain because it has generally been the case that at lower (inferior) vertebral levels, standard SCS treatment produces undesirable side effects, and/or is less efficacious. Such side effects include unwanted muscle activation and/or pain. Once the leads 110 were implanted, the patients received standard SCS treatment for a period of five days. This treatment included stimulation at a frequency of less than 1500 Hz (e.g., 60-80 Hz), a pulse width of 100-200 μsec, and a duty cycle of 100%. The amplitude of the signal (e.g., the current amplitude) was varied from about 3 mA to about 10 mA. The amplitude was initially established during the implant procedure. The amplitude was then changed by the patient on an as-desired basis during the course of the study, as is typical for standard SCS therapies.

After the patient completed the standard SCS portion of the study, the patient then received modulation in accordance with the presently disclosed techniques. One aspect of these techniques included moving the leads 110 inferiorly, so as to be located at vertebral levels T9, T10, T11, and/or T12. After the leads 110 were repositioned, the patient received therapeutic signals at a frequency of from about 3 kHz to about 10 kHz. In particular cases, the therapy was applied at 8 kHz, 9 kHz or 10 kHz. These frequencies are significantly higher than the frequencies associated with standard SCS, and accordingly, modulation at these and other representative frequencies (e.g., from about 1.5 kHz to about 100 kHz) is occasionally referred to herein as high frequency modulation. The modulation was applied generally at a duty cycle of from about 50% to about 100%, with the modulation signal on for a period of from about 1 msec. to about 2 seconds, and off for a period of from about 1 msec. to about 1.5 seconds. The width of the applied pulses was about 30-35 μsec., and the amplitude generally varied from about 1 mA to about 4 mA (nominally about 2.5 mA). Modulation in accordance with the foregoing parameters was typically applied to the patients for a period of about four days during the initial clinical study.

Figure 2:
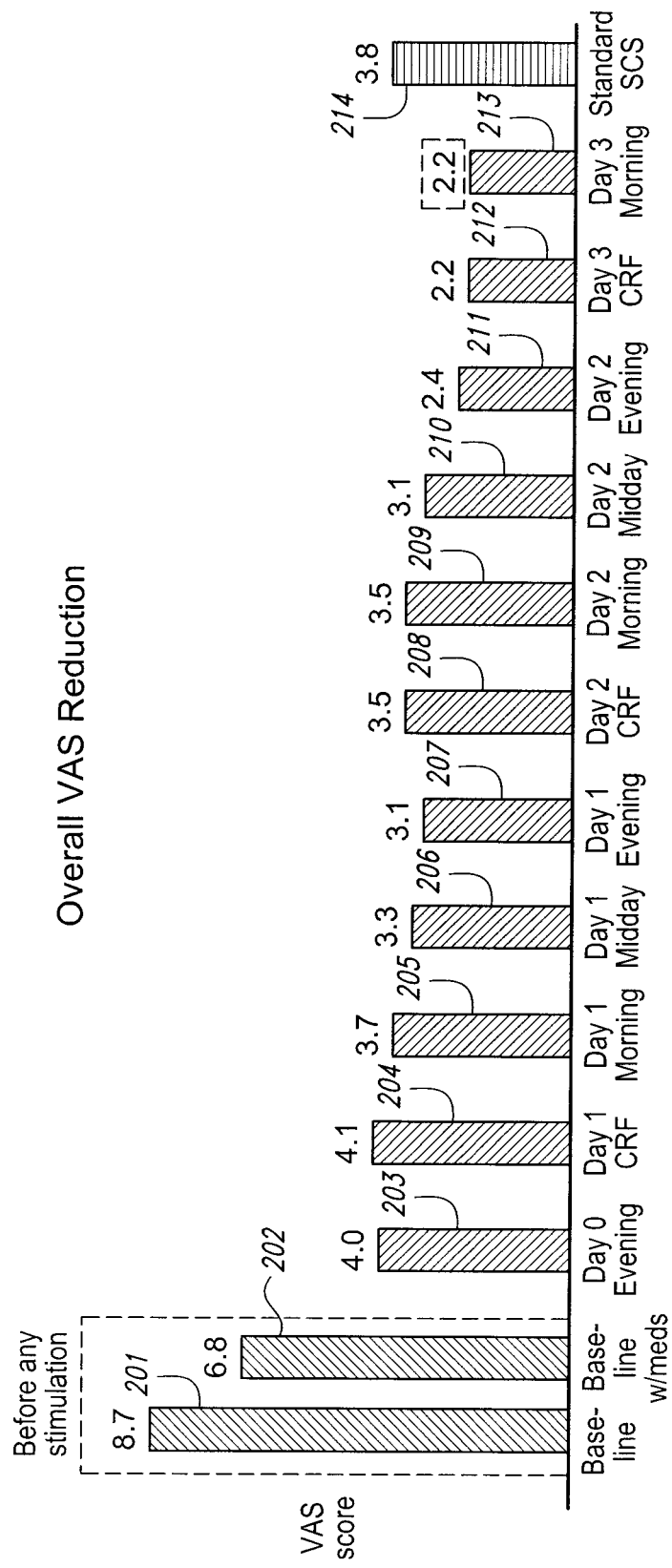
FIG. 2 is a bar chart illustrating pain reduction levels for patients over a four day period of a clinical study, during which the patients received therapy in accordance with an embodiment of the disclosure, as compared with baseline levels and levels achieved with conventional spinal cord stimulation devices.

FIGS. 2-6A graphically illustrate summaries of the clinical results obtained by testing patients in accordance with the foregoing parameters. FIG. 2 is a bar chart illustrating the patients' Visual Analog Scale (VAS) pain score for a variety of conditions. The scores indicated in FIG. 2 are for overall pain. As noted above, these patients suffered primarily from low back pain and accordingly, the pain scores for low back pain alone were approximately the same as those shown in FIG. 2. Each of the bars represents an average of the values reported by the multiple patients involved in this portion of the study. Bars 201 and 202 illustrate a baseline pain level of 8.7 for the patients without the benefit of medication, and a baseline level of 6.8 with medication, respectively. After receiving a lead implant on day zero of the study, and initiating high frequency modulation in accordance with the foregoing parameters, patients reported an average pain score of about 4.0, as represented by bar 203. Over the course of the next three days, (represented by bars 204-213) the patients recorded pain levels in a diary every morning, midday and evening, as indicated by the correspondingly labeled bars in FIG. 2. In addition, pain levels were recorded daily by the local center research coordinator on case report forms (CRFs) as indicated by the correspondingly labeled bars in FIG. 2. During this time period, the patients' average pain score gradually decreased to a reported minimum level of about 2.2 (represented by bars 212 and 213).

For purposes of comparison, bar 214 illustrates the pain score for the same patients receiving standard SCS therapy earlier in the study. Bar 214 indicates that the average pain value for standard SCS therapy was 3.8. Unlike the results of the presently disclosed therapy, standard SCS therapy tended to produce relatively flat patient pain results over the course of several days. Comparing bars 213 and 214, the clinical results indicate that the presently disclosed therapy reduced pain by 42% when compared with standard SCS therapy.

Other pain indices indicated generally consistent results. On the Oswestry Disability Index, average scores dropped from a baseline value of 54 to a value of 33, which is equivalent to a change from "severe disability" to "moderate disability". Patients' global improvement scores ranked 1.9 on a scale of 1 ("very much improved") to 7 ("very much worse").

Figure 3:
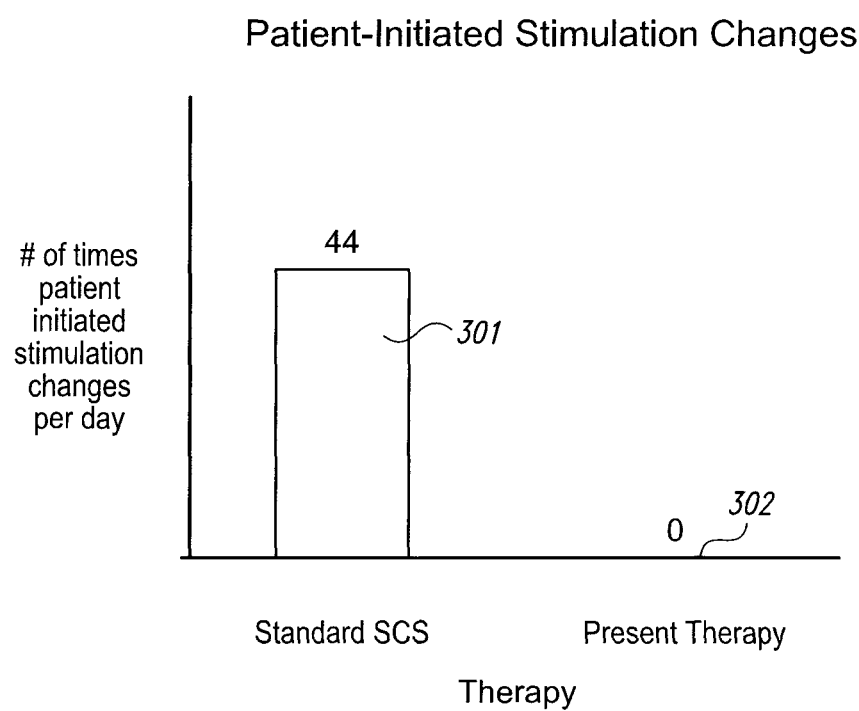
FIG. 3 is a bar chart comparing the number of times patients receiving therapy in accordance with an embodiment of the present disclosure during a clinical study initiated modulation changes, as compared with similar data for patients receiving conventional spinal cord stimulation.

In addition to obtaining greater pain relief with the presently disclosed therapy than with standard SCS therapy, patients experienced other benefits as well, described further below with reference to FIGS. 3-5C. FIG. 3 is a bar chart illustrating the number of times per day that the patients initiated modulation changes. Results are illustrated for standard SCS therapy (bar 301) and the presently disclosed therapy (bar 302). The patient-initiated modulation changes were generally changes in the amplitude of the applied signal, and were initiated by the patient via an external modulator or remote, such as was described above with reference to FIG. 1A. Patients receiving standard SCS therapy initiated changes to the signal delivery parameters an average of 44 times per day. The initiated changes were typically triggered when the patient changed position, activity level, and/or activity type, and then experienced a reduction in pain relief and/or an unpleasant, uncomfortable, painful, unwanted or unexpected sensation from the therapeutic signal. Patients receiving the presently disclosed therapy did not change the signal delivery parameters at all, except at the practitioners' request. In particular, the patients did not change signal amplitude to avoid painful stimulation. Accordingly, FIG. 3 indicates that the presently disclosed therapy is significantly less sensitive to lead movement, patient position, activity level and activity type than is standard SCS therapy.

Figure 4:
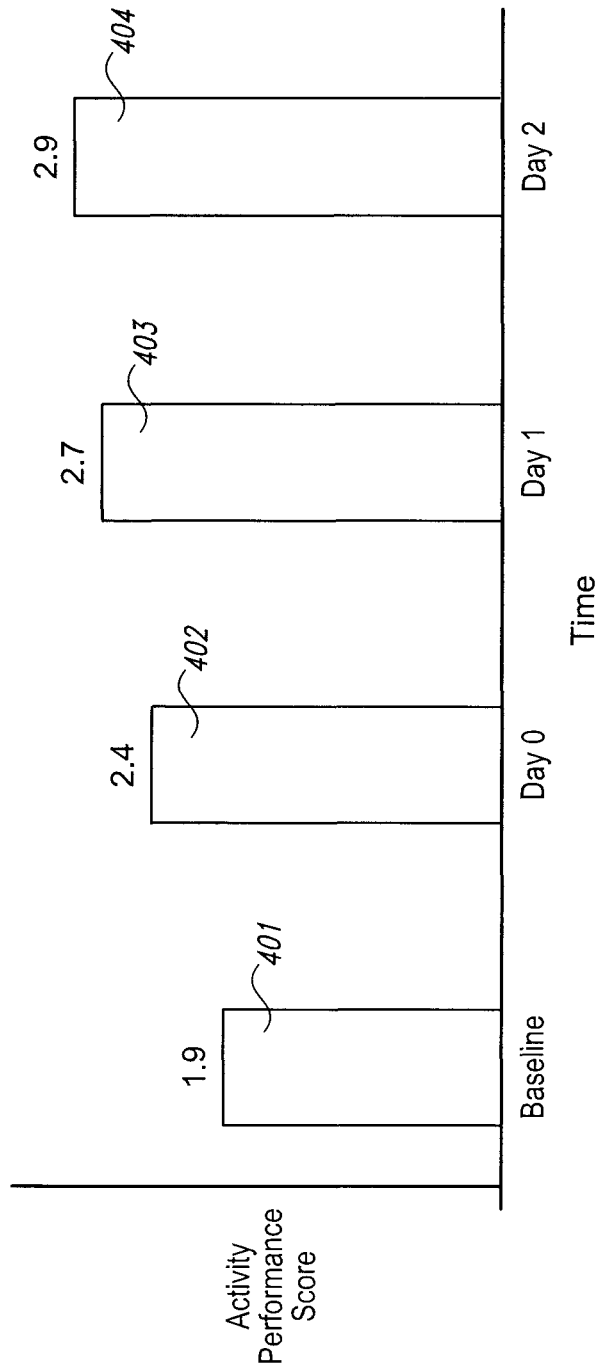
FIG. 4 is a bar chart illustrating activity performance improvements for patients receiving therapy in accordance with an embodiment of the disclosure, obtained during a clinical study.

FIG. 4 is a bar graph illustrating activity scores for patients receiving the presently disclosed therapy. The activity score is a quality of life score indicating generally the patients' level of satisfaction with the amount of activity that they are able to undertake. As indicated in FIG. 4, bar 401 identifies patients having a score of 1.9 (e.g., poor to fair) before beginning therapy. The score improved over time (bars 402-404) so that at the end of the second day of therapy, patients reported a score of nearly 3 (corresponding to a score of "good"). It is expected that in longer studies, the patients' score may well improve beyond the results shown in FIG. 4. Even the results shown in FIG. 4, however, indicate a 53% improvement (compared to baseline) in the activity score for patients receiving the presently disclosed therapy over a three day period. Anecdotally, patients also indicated that they were more active when receiving the presently disclosed therapy than they were when receiving standard SCS therapy. Based on anecdotal reports, it is expected that patients receiving standard SCS therapy would experience only a 10-15% improvement in activity score over the same period of time.

Figure 5A:
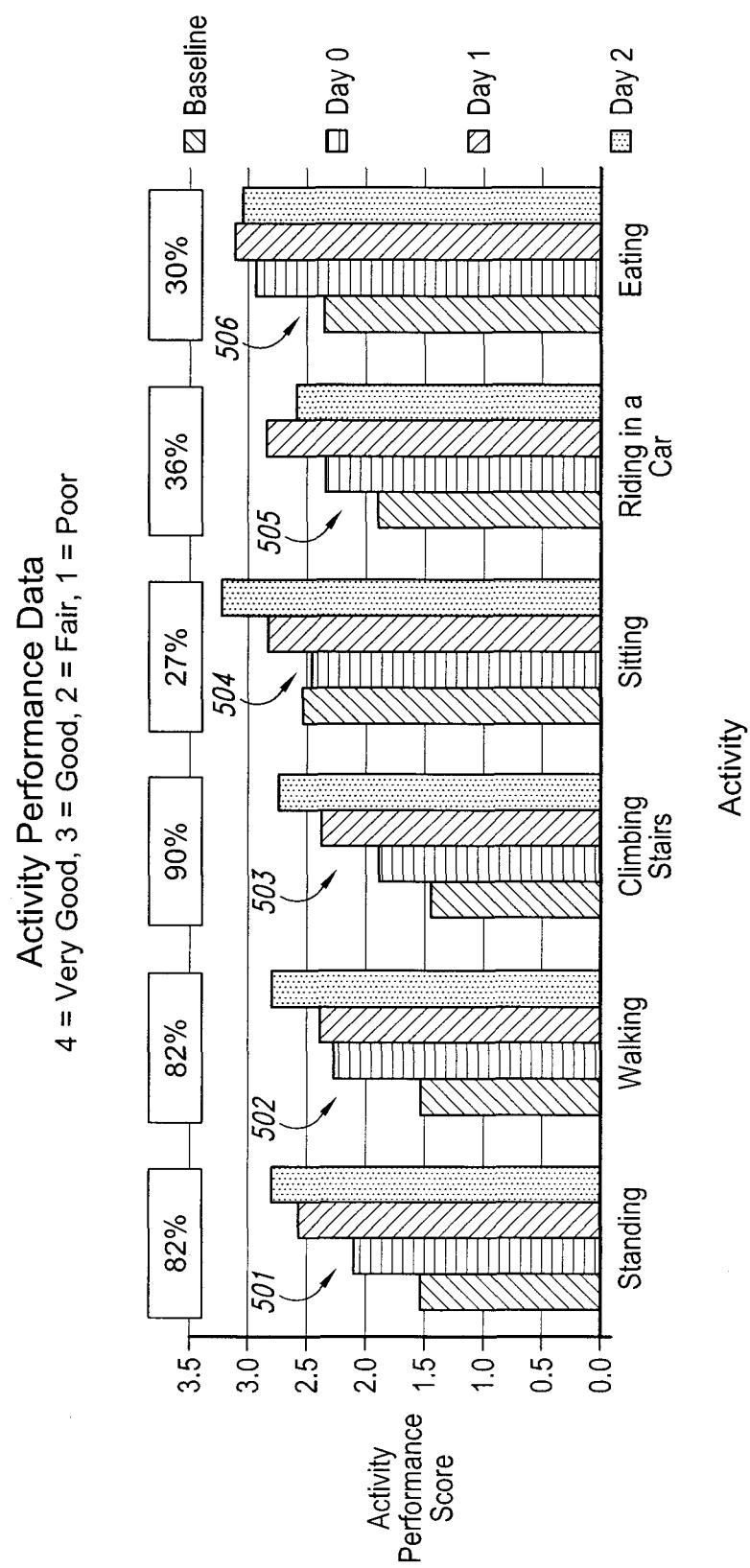
FIG. 5A is a bar chart comparing activity performance levels for patients performing a variety of activities, obtained during a clinical study.

FIG. 5A is a bar chart illustrating changes in activity score for patients receiving the presently disclosed therapy and performing six activities: standing, walking, climbing, sitting, riding in a car, and eating. For each of these activities, groups of bars (with individual groups identified by reference numbers 501, 502, 503 . . . 506) indicate that the patients' activity score generally improved over the course of time. These results further indicate that the improvement in activity was broad-based and not limited to a particular activity. Still further, these results indicate a significant level of improvement in each activity, ranging from 30% for eating to 80%-90% for standing, walking and climbing stairs. Anecdotally, it is expected that patients receiving standard SCS treatment would experience only about 10%-20% improvement in patient activity. Also anecdotally, the improvement in activity level was directly observed in at least some patients who were hunched over when receiving standard SCS treatment, and were unable to stand up straight. By contrast, these patients were able to stand up straight and engage in other normal activities when receiving the presently disclosed therapy.

Figures 5B, 5C:
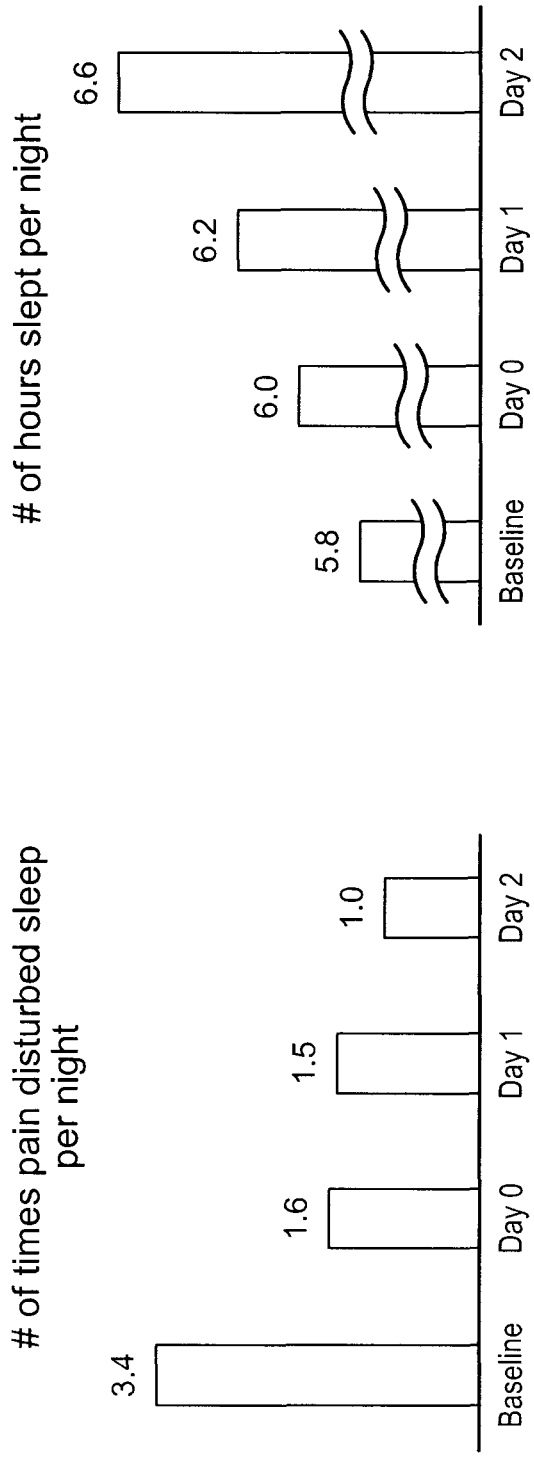
FIGS. 5B and 5C are bar charts illustrating sleep improvement for patients receiving therapy in accordance with embodiments of the disclosure, obtained during a clinical study.

The improvement experienced by the patients is not limited to improvements in activity but also extends to relative inactivity, including sleep. For example, patients receiving standard SCS therapy may establish a signal delivery parameter at a particular level when lying prone. When the patient rolls over while sleeping, the patient may experience a significant enough change in the pain reduction provided by standard SCS treatments to cause the patient to wake. In many cases, the patient may additionally experience pain generated by the SCS signal itself, on top of the pain the SCS signal is intended to reduce. Accordingly, the accepted procedure for many conventional SCS systems is to turn the therapy off while the patient is sleeping. With the presently disclosed techniques, by contrast, the foregoing undesirable effects and/or limitations can be avoided. FIGS. 5B and 5C illustrate the average effect on sleep for clinical patients receiving the presently disclosed therapy. FIG. 5B illustrates the reduction in patient disturbances, and FIG. 5C illustrates the increase in number of hours slept. In other embodiments, the patient may be able to perform other tasks with reduced pain. For example, patients may drive without having to adjust the therapy level provided by the implanted device. Accordingly, the presently disclosed therapy may be more readily used by patients in such situations and/or other situations that improve the patients' quality of life.

Based on additional patient feedback, every one of the tested patients who received the presently disclosed therapy at the target location (e.g., who received the presently disclosed therapy without the lead migrating significantly from its intended location) preferred the presently disclosed therapy to standard SCS therapy. In addition, irrespective of the level of pain relief the patients received, 88% of the patients preferred the presently disclosed therapy to standard SCS therapy because it reduced their pain without creating paresthesia. This indicates that while patients may prefer paresthesia to pain, a significant majority prefer no sensation to both pain and paresthesia. This result, obtained via the presently disclosed therapy, is not available with standard SCS therapies that are commonly understood to rely on paresthesia (i.e., masking) to produce pain relief.

Still further, anecdotal data indicate that patients receiving the presently disclosed therapy experienced less, e.g., significantly less muscle capture than they experienced with standard SCS. In particular, patients reported a lack of spasms, cramps, and muscle pain, some or all of which they experienced when receiving standard SCS. Patients also reported no interference with volitional muscle action, and instead indicated that they were able to perform motor tasks unimpeded by the presently disclosed therapy. Still further, patients reported no interference with other sensations, including sense of touch (e.g., detecting vibration), temperature and proprioception. In most cases, patients reported no interference with nociceptive pain sensation. However, in some cases, patients reported an absence of incision pain (associated with the incision used to implant the signal delivery lead) or an absence of chronic peripheral pain (associated with arthritis). Accordingly, in particular embodiments, aspects of the currently disclosed techniques may be used to address nociceptive pain, including acute peripheral pain, and/or chronic peripheral pain. For example, in at least some cases, patients with low to moderate nociceptive pain received relief as a result of the foregoing therapy. Patients with more severe/ chronic nociceptive pain were typically not fully responsive to the present therapy techniques. This result may be used in a diagnostic setting to distinguish the types of pain experienced by the patients, as will be discussed in greater detail later.

Figure 6A:
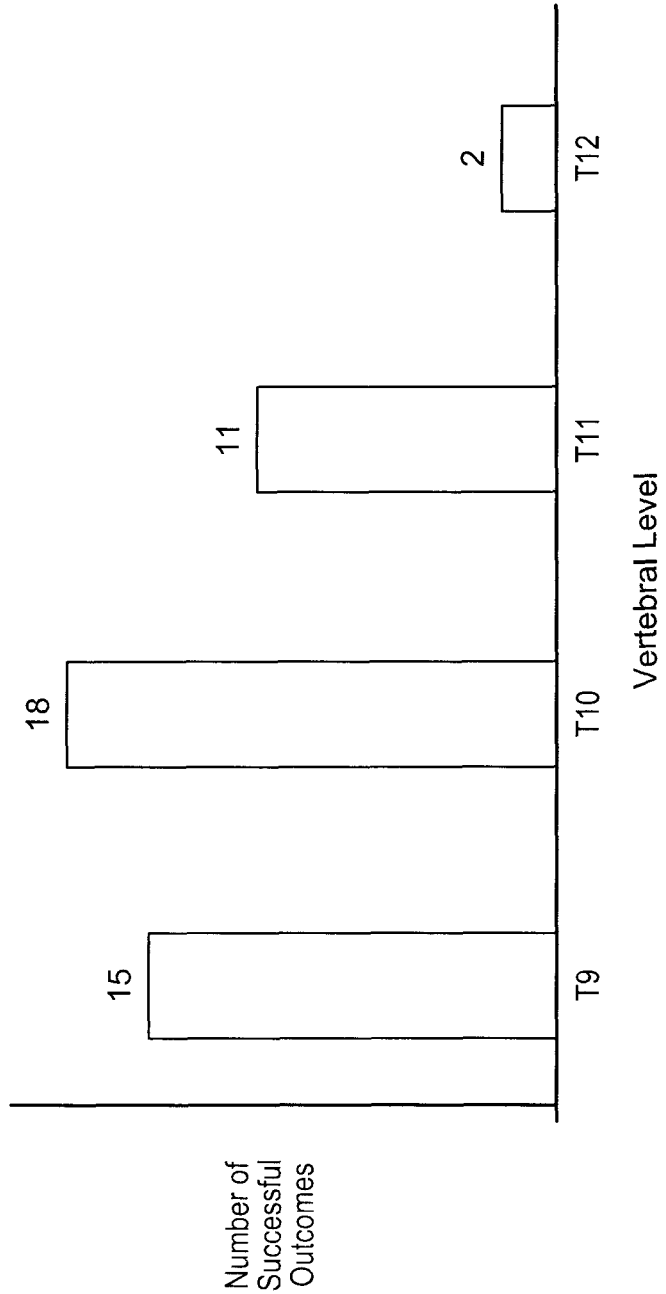
FIG. 6A is a bar chart illustrating successful therapy outcomes as a function of modulation location for patients receiving therapy in accordance with an embodiment of the disclosure, obtained during a clinical study.

FIG. 6A is a bar chart indicating the number of successful therapeutic outcomes as a function of the location (indicated by vertebral level) of the active contacts on the leads that provided the presently disclosed therapy. In some cases, patients obtained successful outcomes when modulation was provided at more than one vertebral location. As indicated in FIG. 6A, successful outcomes were obtained over a large axial range (as measured in a superior-inferior direction along the spine) from vertebral bodies T9 to T12. This is a surprising result in that it indicates that while there may be a preferred target location (e.g., around T10), the lead can be positioned at a wide variety of locations while still producing successful results. In particular, neighboring vertebral bodies are typically spaced apart from each other by approximately 32 millimeters (depending on specific patient anatomy), and so successful results were obtained over a broad range of four vertebral bodies (about 128 mm.) and a narrower range of one to two vertebral bodies (about 32-64 mm.). In other embodiments, the range can be more limited, e.g., about 12 mm in the axial direction. By contrast, standard SCS data generally indicate that the therapy may change from effective to ineffective with a shift of as little as 1 mm. in lead location. As will be discussed in greater detail later, the flexibility and versatility associated with the presently disclosed therapy can produce significant benefits for both the patient and the practitioner.

Figure 6B:
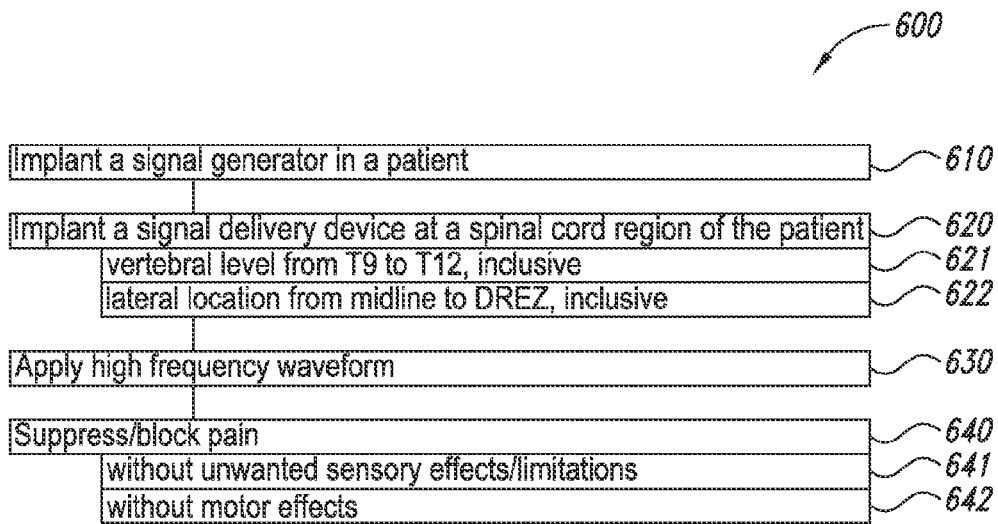
FIGS. 6B and 6C are flow diagrams illustrating methods conducted in accordance with embodiments of the disclosure.
Figure 6C:
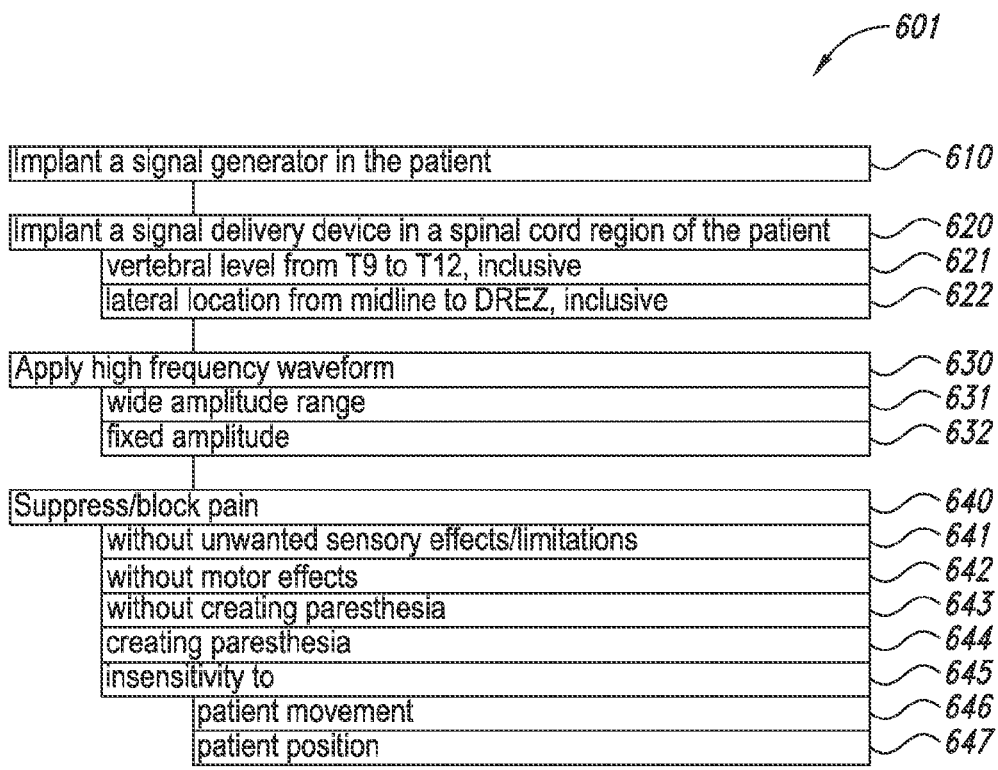

FIGS. 6B and 6C are flow diagrams illustrating methods for treating patients in accordance with particular embodiments of the present disclosure. Manufacturers or other suitable entities can provide instructions to practitioners for executing these and other methods disclosed herein. Manufacturers can also program devices of the disclosed systems to carry out at least some of these methods. FIG. 6B illustrates a method 600 that includes implanting a signal generator in a patient (block 610). The signal generator can be implanted at the patient's lower back or other suitable location. The method 600 further includes implanting a signal delivery device (e.g., a lead, paddle or other suitable device) at the patient's spinal cord region (block 620). This portion of the method can in turn include implanting the device (e.g., active contacts of the device) at a vertebral level ranging from about T9 to about T12 (e.g., about T9-T12, inclusive) (block 621), and at a lateral location ranging from the spinal cord midline to the DREZ, inclusive (block 622). At block 630, the method includes applying a high frequency waveform, via the signal generator and the signal delivery device. In particular examples, the frequency of the signal (or at least a portion of the signal) can be from about 1.5 kHz to about 100 kHz, or from about 1.5 kHz to about 50 kHz., or from about 3 kHz to about 20 kHz, or from about 3 kHz to about 15 kHz, or from about 5 kHz to about 15 kHz, or from about 3 kHz to about 10 kHz. The method 600 further includes blocking, suppressing, inhibiting or otherwise reducing the patient's pain, e.g., chronic low back pain (block 640). This portion of the method can in turn include reducing pain without unwanted sensory effects and/or limitations (block 641), and/or without motor effects (block 642). For example, block 641 can include reducing or eliminating pain without reducing patient perception of other sensations, and/or without triggering additional pain. Block 642 can include reducing or eliminating pain without triggering muscle action and/or without interfering with motor signal transmission.

FIG. 6C illustrates a method 601 that includes features in addition to those described above with reference to FIG. 6B. For example, the process of applying a high frequency waveform (block 630) can include doing so over a wide amplitude range (e.g., from less than 1 mA up to about 8 mA in one embodiment, and up to about 6 mA and about 5 mA, respectively, in other embodiments) without creating unwanted side effects, such as undesirable sensations and/or motor interference (block 631). In another embodiment, the process of applying a high frequency waveform can include applying the waveform at a fixed amplitude (block 632). As described further later, each of these aspects can provide patient and/or practitioner benefits.

The process of blocking, suppressing or otherwise reducing patient pain (block 640) can include doing so without creating paresthesia (block 643), or in association with a deliberately generated paresthesia (block 644). As noted above, clinical results indicate that most patients prefer the absence of paresthesia to the presence of paresthesia, e.g., because the sensation of paresthesia may change to an uncomfortable or painful sensation when the patient changes position and/or adjusts the signal amplitude. However, in some cases, patients may prefer the sensation of paresthesia (e.g., patients who have previously received SCS), and so can have the option of receiving it. Further details of methodologies that include combinations of paresthesia-inducing modulation and non-paresthesia-inducing modulation are included in U.S. application Ser. No. 12/765,685, incorporated herein by reference. In other cases, paresthesia may be used by the practitioner for site selection (e.g., to determine the location at which active electrodes are positioned). In addition to the above, reducing patient pain can include doing so with relative insensitivity to patient attributes that standard SCS is normally highly sensitive to (block 645). These attributes can include patient movement (block 646) and/or patient position (block 647).

2.2. Follow-on Study

Nevro Corporation, the assignee of the present application, has conducted a follow-on study to evaluate particular parameters and results of the therapy described above. In the follow-on study, patients received implanted leads and simulators, and received therapy over a period of several months. This study did not include a direct comparison with conventional SCS techniques for each patient, though some of the patients received conventional SCS therapy prior to receiving modulation in accordance with the present technology. Selected results are described further below.

Figure 7A:
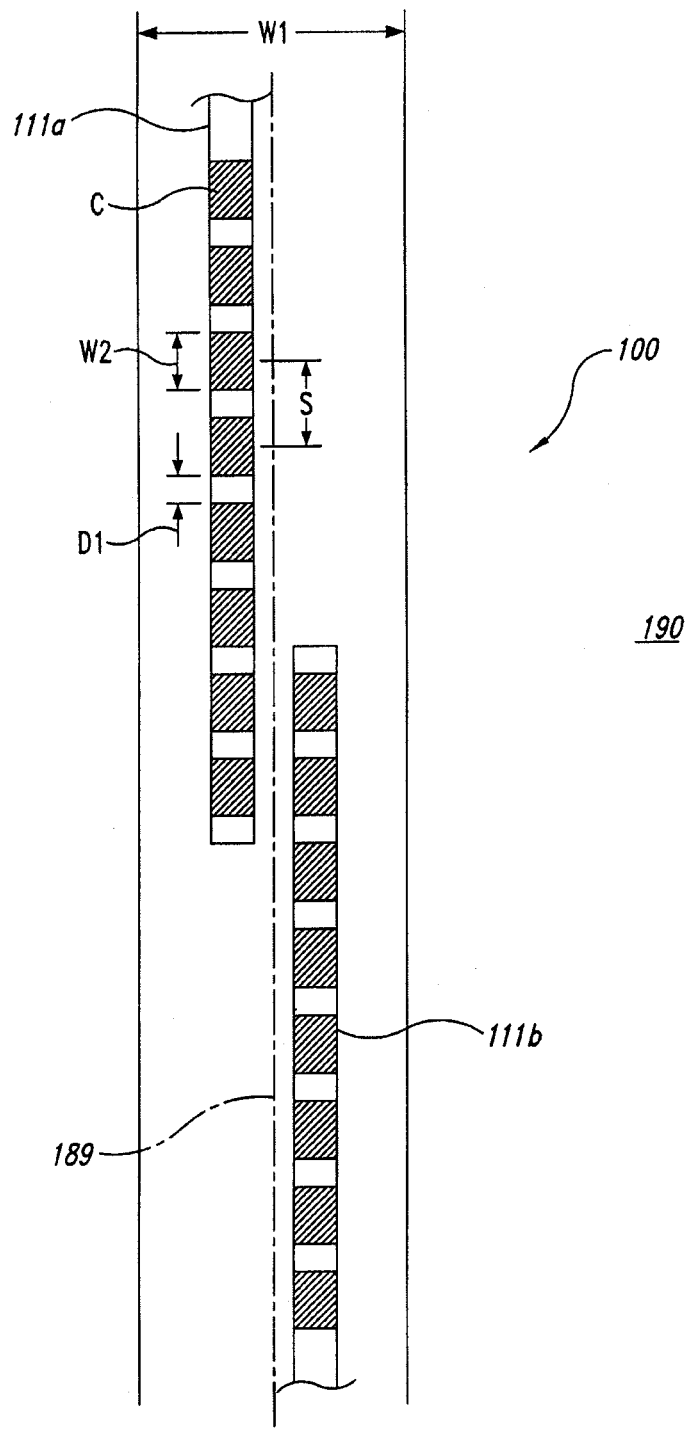
FIG. 7A illustrates an arrangement of leads used during a follow-on clinical study in accordance with an embodiment of the disclosure.

FIG. 7A is a schematic illustration of a typical lead placement used during the follow-on study. In this study, two leads 111 (shown as a first lead 111a and a second lead 111b) were positioned generally end-to-end to provide a modulation capability that extends over several vertebral levels of the patients' spine. The leads 111a, 111b were positioned to overlap slightly, to account for possible shifts in lead location. During the course of the therapy, contacts C of the two leads 111a, 111b were activated on one lead at a time. In other words, the contacts C of only one lead 111 were active at any one time, and signals were not directed between the contacts C located on different leads 111. While two leads were used during the clinical study, it is expected that in general use, a single lead can be positioned at the appropriate vertebral level. The lead can have more widely spaced contacts to achieve the same or similar effects as those described herein as will be described in greater detail below with reference to FIG. 9.

The contacts C of each lead 111a, 111b have a width W2 of approximately 3 mm, and are separated from each other by a distance D1 of approximately 1 mm. Accordingly, the center-to-center spacing S between neighboring contacts C is approximately 4 mm. The leads 111a, 111b were positioned at or close to the patients' spinal midline 189. Typically, one lead was positioned on one side of the midline 189, and the other lead was positioned on the other side of the patients' midline 189. During the course of the study, several significant effects were observed. For example, the leads 111a, 111b could be positioned at any of a variety of locations within a relatively wide window W1 having an overall width of ±3-5 mm from the midline 189 (e.g., an overall width of 6-10 mm), without significantly affecting the efficacy of the treatment. In addition, patients with bilateral pain (e.g., on both sides of the midline 189) reported bilateral relief, independent of the lateral location of the leads 110a, 110b. For example, patients having a lead located within the window W1 on one side of the midline 189 reported pain relief on the opposite side of the midline 189. This is unlike conventional SCS therapies, for which bilateral relief, when it is obtained at all, is generally very sensitive to any departure from a strictly midline lead location. Still further, the distance between neighboring active contacts was significantly greater than is typical for standard SCS. Practitioners were able to "skip" (e.g., deactivate) several consecutive contacts so that neighboring active contacts had a center-to-center spacing of, for example, 20 mm, and an edge-to-edge spacing of, for example, 17 mm. In addition, patients were relatively insensitive to the axial location of the active contacts. For example, practitioners were able to establish the same or generally the same levels of pain relief over a wide range of contact spacings that is expected to extend up to two vertebral bodies (e.g., about 64 mm). Yet further, the practitioners obtained a similar therapeutic effect whether a given contact was identified as cathodic or anodic, as is described in greater detail in pending U.S. application Ser. No. 12/765,790, filed on Apr. 22, 2010 and incorporated herein by reference.

For most patients in the follow-on study, the leads were implanted at the T9-T10 vertebral locations. These patients typically experienced primarily low back pain prior to receiving the therapy, though some experienced leg pain as well. Based on the results obtained during the follow-on study and the initial study, it is expected that the overall vertebral location range for addressing low back pain is from about T9 to about T12. In other embodiments, the location can be T11, T9-T11 or T8-T12. It is further expected that within this range, modulation at T12 or T11-T12 may more effectively treat patients with both low back and leg pain. However, in some cases, patients experienced greater leg pain relief at higher vertebral locations (e.g., T9-T10) and in still further particular cases, modulation at T9 produced more leg pain relief than modulation at T10. Accordingly, within the general ranges described above, particular patients may have physiological characteristics or other factors that produce corresponding preferred vertebral locations.

Patients receiving treatment in the follow-on study received a square-wave signal at a frequency of about 10 kHz. Patients received modulation at a 100% duty cycle, with an initial current amplitude (bi-phasic) of about 2 mA. Patients and practitioners were able to adjust the signal amplitude, typically up to about 5 mA. At any of the foregoing levels, the signal pulses are expected to be suprathreshold, meaning that they can trigger an action potential in the target neural population, independent of any intrinsic neural activity at the target neural population.

Patients in the follow-on study were evaluated periodically after the modulation system 100 was implanted and activated. The VAS scores reported by these patients after 30 days of receiving treatment averaged about 1.0, indicating that the trend discussed above with respect to FIG. 2 continued for some period of time. At least some of these patients reported an increase in the VAS score up to level of about 2.25. It is expected that this increase resulted from the patients' increased activity level. Accordingly, it is not believed that this increase indicates a reduction in the efficacy of the treatment, but rather, indicates an effective therapy that allows patients to engage in activities they otherwise would not.

Figure 7B:
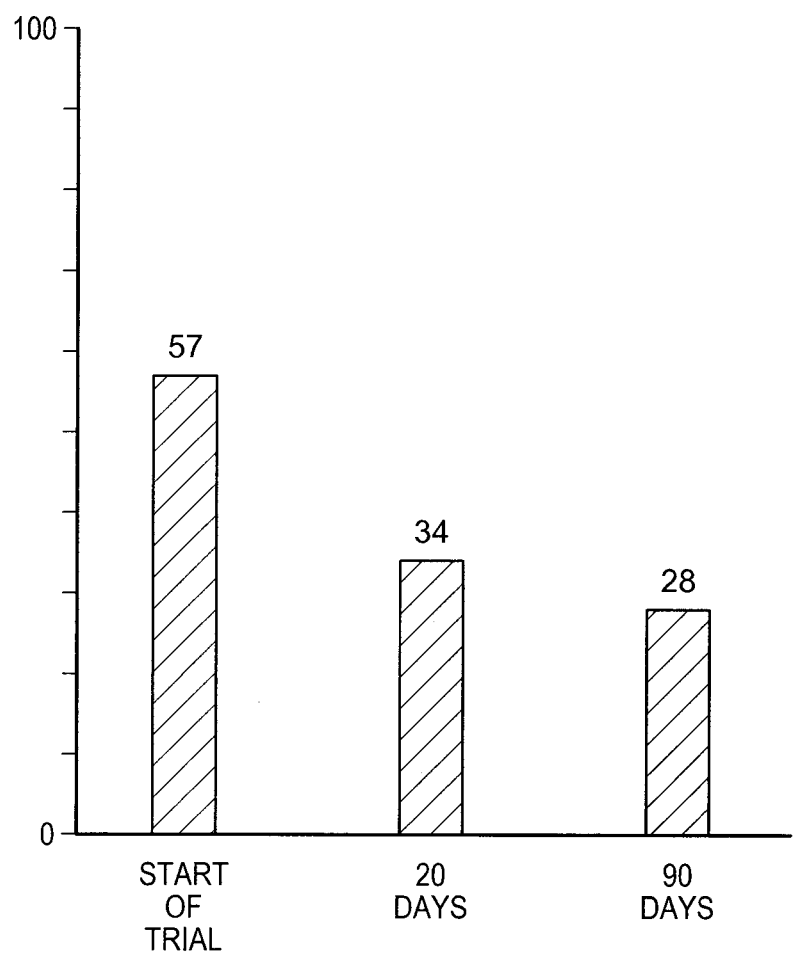
FIG. 7B illustrates results obtained from a follow-on clinical study of patients receiving therapy in accordance with an embodiment of the disclosure.

FIG. 7B illustrates overall Oswestry scores for patients engaging in a variety of activities and receiving modulation in accordance with the follow-on study protocol. A score of 100 corresponds to a completely disabled condition, and a score of 0 corresponds to no disability. These scores indicate a general improvement over time, for example, consistent with and in fact improved over results from in the initial study. In addition, several patients reported no longer needing or using canes or wheelchairs after receiving therapy in accordance with the foregoing embodiments.

Results from the follow-on study confirm a relative insensitivity of the therapeutic effectiveness of the treatment to changes in current amplitude. In particular, patients typically received modulation at a level of from about 2.0 mA to about 3.5 mA. In most cases, patients did not report significant changes in pain reduction when they changed the amplitude of the applied signal. Patients were in several cases able to increase the current amplitude up to a level of about 5 mA before reporting undesirable side effects. In addition, the side effects began to take place in a gradual, rather than a sudden, manner. Anecdotal feedback from some patients indicated that at high amplitudes (e.g., above 5 mA) the treatment efficacy began to fall off, independent of the onset of any undesirable side effects. It is further expected that patients can receive effective therapy at current amplitudes of less than 2 mA. This expectation is based at least in part on data indicating that reducing the duty cycle (e.g., to 70%) did not reduce efficacy.

The results of the follow-on study also indicated that most patients (e.g., approximately 80% of the patients) experienced at least satisfactory pain reduction without changing any aspect of the signal delivery parameters (e.g., the number and/or location of active contacts, and/or the current amplitude), once the system was implanted and activated. A small subset of the patients (e.g., about 20%) benefited from an increased current amplitude when engaging in particular activities, and/or benefited from a lower current amplitude when sleeping. For these patients, increasing the signal amplitude while engaging in activity produced a greater degree of pain relief, and reducing the amplitude at night reduced the likelihood of over-stimulation, while at the same time saving power. In a representative example, patients selected from between two such programs: a "strong" program which provided signals at a relatively high current amplitude (e.g., from about 1 mA to about 6 mA), and a "weak" program which provided signals at a lower current amplitude (e.g., from about 0.1 mA to about 3 mA).

Another observed effect during the follow-on study was that patients voluntarily reduced their intake of opioids and/or other pain medications that they had been receiving to address pain prior to receiving modulation in accordance with the present technology. The patients' voluntary drug intake reduction is expected to be a direct result of the decreased need for the drugs, which is in turn a direct result of the modulation provided in accordance with the present technology. However, due to the addictive nature of opioids, the ease with which patients voluntarily gave up the use of opioids was surprising. Therefore, it is also expected that for at least some patients, the present technology, in addition to reducing pain, acted to reduce the chemical dependency on these drugs. Accordingly, it is further expected that in at least some embodiments, therapeutic techniques in accordance with the present disclosure may be used to reduce or eliminate patient chemical dependencies, independent of whether the patients also have and/or are treated for low back pain.

Patients entering the follow-on study typically experienced neuropathic pain, nociceptive pain, or a combination of neuropathic pain and nociceptive pain. Neuropathic pain refers generally to pain resulting from a dysfunction in the neural mechanism for reporting pain, which can produce a sensation of pain without an external neural trigger. Nociceptive pain refers generally to pain that is properly sensed by the patient as being triggered by a particular mechanical or other physical effect (e.g., a slipped disc, a damaged muscle, or a damaged bone). In general, neuropathic pain is consistent, and nociceptive pain fluctuates, e.g., with patient position or activity. In at least some embodiments, treatment in accordance with the present technology appears to more effectively address neuropathic pain than nociceptive pain. For example, patients who reported low levels of pain fluctuation before entering treatment (indicating predominantly neuropathic pain), received greater pain relief during treatment than patients whose pain fluctuated significantly. In two particular cases, the therapy did not prove to be effective, and it is believe that this resulted from a mechanical issue with the patients' back anatomy, which identified the patients as better candidates for surgery than for the present therapy. Accordingly, in addition to addressing neuropathic pain and (in at least some cases), nociceptive pain, techniques in accordance with the present technology may also act as a screening tool to identify patients who suffer primarily from nociceptive pain rather than neuropathic pain. For example, the practitioner can make such an identification based at least in part on feedback from the patient corresponding to the existence and/or amount (including amount of fluctuation) of pain reduction when receiving signals in accordance with the present technology. As a result of using this diagnostic technique, these patients can be directed to surgical or other procedures that can directly address the nociceptive pain. In particular, patients may receive signals in accordance with the present technology and, if these patients are unresponsive, may be suitable candidates for surgical intervention. Of course, if the patients are responsive, they can continue to receive signals in accordance with the present technology as therapy.

3.0 Mechanisms of Action

Figure 8:
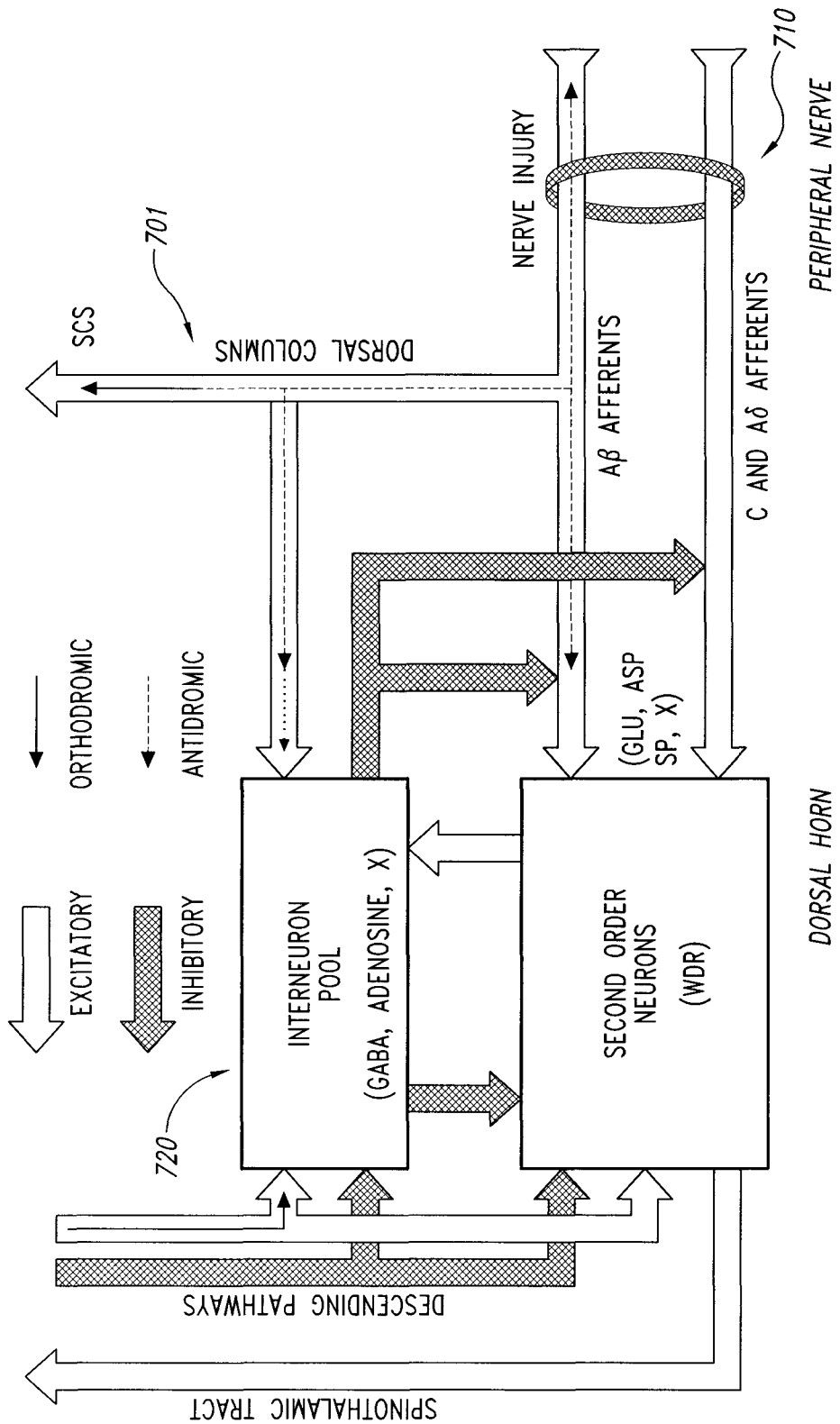
FIG. 8 is a schematic illustration identifying possible mechanisms of action for therapies in accordance with the present disclosure, as compared with an expected mechanism of action for conventional spinal cord stimulation.

FIG. 8 is a schematic diagram (based on Linderoth and Foreman, "Mechanisms of Spinal Cord Stimulation in Painful Syndromes: Role of Animal Models," Pain Medicine, Vol. 51, 2006) illustrating an expected mechanism of action for standard SCS treatment, along with potential mechanisms of action for therapy provided in accordance with embodiments of the present technology. When a peripheral nerve is injured, it is believed that the Aδ and C nociceptors provide an increased level of excitatory transmitters to second order neurons at the dorsal horn of the spinal cord. Standard SCS therapy, represented by arrow 701, is expected to have two effects. One effect is an orthodromic effect transmitted along the dorsal column to the patient's brain and perceived as paresthesia. The other is an antidromic effect that excites the interneuron pool, which in turn inhibits inputs to the second order neurons.

One potential mechanism of action for the presently disclosed therapy is represented by arrow 710, and includes producing an incomplete conduction block (e.g., an incomplete block of afferent and/or efferent signal transmission) at the dorsal root level. This block may occur at the dorsal column, dorsal horn, and/or dorsal root entry zone, in addition to or in lieu of the dorsal root. In any of these cases, the conduction block is selective to and/or preferentially affects the smaller Aδ and/or C fibers and is expected to produce a decrease in excitatory inputs to the second order neurons, thus producing a decrease in pain signals supplied along the spinal thalamic tract.

Another potential mechanism of action (represented by arrow 720 in FIG. 8) includes more profoundly activating the interneuron pool and thus increasing the inhibition of inputs into the second order neurons. This can, in effect, potentially desensitize the second order neurons and convert them closer to a normal state before the effects of the chronic pain associated signals have an effect on the patient.

Still another potential mechanism of action relates to the sensitivity of neurons in patients suffering from chronic pain. In such patients, it is believed that the pain-transmitting neurons may be in a different, hypersensitive state compared to the same neurons in people who do not experience chronic pain, resulting in highly sensitized cells that are on a "hair trigger" and fire more frequently and at different patterns with a lower threshold of stimulation than those cells of people who do not experience chronic pain. As a result, the brain receives a significantly increased volume of action potentials at significantly altered transmission patterns. Accordingly, a potential mechanism of action by which the presently disclosed therapies may operate is by reducing this hypersensitivity by restoring or moving the "baseline" of the neural cells in chronic pain patients toward the normal baseline and firing frequency of non-chronic pain patients. This effect can in turn reduce the sensation of pain in this patient population without affecting other neural transmissions (for example, touch, heat, etc.).

The foregoing mechanisms of action are identified here as possible mechanisms of action that may account for the foregoing clinical results. In particular, these mechanisms of action may explain the surprising result that pain signals transmitted by the small, slow A$\delta$ and C fibers may be inhibited without affecting signal transmission along the larger, faster A$\beta$ fibers. This is contrary to the typical results obtained via standard SCS treatments, during which modulation signals generally affect A$\beta$ fibers at low amplitudes, and do not affect A$\delta$ and C fibers until the signal amplitude is so high as to create pain or other unwanted effects transmitted by the A$\beta$ fibers. However, aspects of the present disclosure need not be directly tied to such mechanisms. In addition, aspects of both the two foregoing proposed mechanisms may in combination account for the observed results in some embodiments, and in other embodiments, other mechanisms may account for the observed results, either alone or in combination with either one of the two foregoing mechanisms. One such mechanism includes an increased ability of high frequency modulation (compared to standard SCS stimulation) to penetrate through the cerebral spinal fluid (CSF) around the spinal cord. Another such mechanism is the expected reduction in impedance presented by the patient's tissue to high frequencies, as compared to standard SCS frequencies. Still another such mechanism is the ability of high frequency signal to elicit an asynchronous neural response, as disclosed in greater detail in pending U.S. application Ser. No. 12/362,244, filed on Jan. 29, 2009 and incorporated herein by reference. Although the higher frequencies associated with the presently disclosed techniques may initially appear to require more power than conventional SCS techniques, the signal amplitude may be reduced when compared to conventional SCS values (due to improved signal penetration) and/or the duty cycle may be reduced (due to persistence effects described later). Accordingly, the presently disclosed techniques can result in a net power savings when compared with standard SCS techniques.

4.0 Expected Benefits Associated with Certain Embodiments

Certain of the foregoing embodiments can produce one or more of a variety of advantages, for the patient and/or the practitioner, when compared with standard SCS therapies. Some of these benefits were described above. For example, the patient can receive effective pain relief without patient-detectable disruptions to normal sensory and motor signals along the spinal cord. In particular embodiments, while the therapy may create some effect on normal motor and/or sensory signals, the effect is below a level that the patient can reliably detect intrinsically, e.g., without the aid of external assistance via instruments or other devices. Accordingly, the patient's levels of motor signaling and other sensory signaling (other than signaling associated with the target pain) can be maintained at pre-treatment levels. For example, as described above, the patient can experience a significant pain reduction that is largely independent of the patient's movement and position. In particular, the patient can assume a variety of positions and/or undertake a variety of movements associated with activities of daily living and/or other activities, without the need to adjust the parameters in accordance with which the therapy is applied to the patient (e.g., the signal amplitude). This result can greatly simplify the patient's life and reduce the effort required by the patient to experience pain relief while engaging in a variety of activities. This result can also provide an improved lifestyle for patients who experience pain during sleep, as discussed above with reference to FIGS. 5B and 5C.

Even for patients who receive a therapeutic benefit from changes in signal amplitude, the foregoing therapy can provide advantages. For example, such patients can choose from a limited number of programs (e.g., two or three) each with a different amplitude and/or other signal delivery parameter, to address some or all of the patient's pain. In one such example, the patient activates one program before sleeping and another after waking. In another such example, the patient activates one program before sleeping, a second program after waking, and a third program before engaging in particular activities that would otherwise cause pain. This reduced set of patient options can greatly simplify the patient's ability to easily manage pain, without reducing (and in fact, increasing) the circumstances under which the therapy effectively addresses pain. In any embodiments that include multiple programs, the patient's workload can be further reduced by automatically detecting a change in patient circumstance, and automatically identifying and delivering the appropriate therapy regimen. Additional details of such techniques and associated systems are disclosed in co-pending U.S. application Ser. No. 12/703,683, previously incorporated herein by reference.

Another benefit observed during the clinical studies described above is that when the patient does experience a change in the therapy level, it is a gradual change. This is unlike typical changes associated with conventional SCS therapies. With conventional SCS therapies, if a patient changes position and/or changes an amplitude setting, the patient can experience a sudden onset of pain, often described by patients as unbearable. By contrast, patients in the clinical studies described above, when treated with the presently disclosed therapy, reported a gradual onset of pain when signal amplitude was increased beyond a threshold level, and/or when the patient changed position, with the pain described as gradually becoming uncomfortable. One patient described a sensation akin to a cramp coming on, but never fully developing. This significant difference in patient response to changes in signal delivery parameters can allow the patient to more freely change signal delivery parameters and/or posture when desired, without fear of creating an immediately painful effect.

Another observation from the clinical studies described above is that the amplitude "window" between the onset of effective therapy and the onset of pain or discomfort is relatively broad, and in particular, broader than it is for standard SCS treatment. For example, during standard SCS treatment, the patient typically experiences a pain reduction at a particular amplitude, and begins experiencing pain from the therapeutic signal (which may have a sudden onset, as described above) at from about 1.2 to about 1.6 times that amplitude. This corresponds to an average dynamic range of about 1.4. In addition, patients receiving standard SCS stimulation typically wish to receive the stimulation at close to the pain onset level because the therapy is often most effective at that level. Accordingly, patient preferences may further reduce the effective dynamic range. By contrast, therapy in accordance with the presently disclosed technology resulted in patients obtaining pain relief at 1 mA or less, and not encountering pain or muscle capture until the applied signal had an amplitude of 4 mA, and in some cases up to about 5 mA, 6 mA, or 8 mA, corresponding to a much larger dynamic range (e.g., larger than 1.6 or 60% in some embodiments, or larger than 100% in other embodiments). Even at the forgoing amplitude levels, the pain experienced by the patients was significantly less than that associated with standard SCS pain onset. An expected advantage of this result is that the patient and practitioner can have significantly wider latitude in selecting an appropriate therapy amplitude with the presently disclosed methodology than with standard SCS methodologies. For example, the practitioner can increase the signal amplitude in an effort to affect more (e.g., deeper) fibers at the spinal cord, without triggering unwanted side effects. The existence of a wider amplitude window may also contribute to the relative insensitivity of the presently disclosed therapy to changes in patient posture and/or activity. For example, if the relative position between the implanted lead and the target neural population changes as the patient moves, the effective strength of the signal when it reaches the target neural population may also change. When the target neural population is insensitive to a wider range of signal strengths, this effect can in turn allow greater patient range of motion without triggering undesirable side effects.

Although the presently disclosed therapies may allow the practitioner to provide modulation over a broader range of amplitudes, in at least some cases, the practitioner may not need to use the entire range. For example, as described above, the instances in which the patient may need to adjust the therapy may be significantly reduced when compared with standard SCS therapy because the presently disclosed therapy is relatively insensitive to patient position, posture and activity level. In addition to or in lieu of the foregoing effect, the amplitude of the signals applied in accordance with the presently disclosed techniques may be lower than the amplitude associated with standard SCS because the presently disclosed techniques may target neurons that are closer to the surface of the spinal cord. For example, it is believed that the nerve fibers associated with low back pain enter the spinal cord between T9 and T12 (inclusive), and are thus close to the spinal cord surface at these vertebral locations. Accordingly, the strength of the therapeutic signal (e.g., the current amplitude) can be modest because the signal need not penetrate through a significant depth of spinal cord tissue to have the intended effect. Such low amplitude signals can have a reduced (or zero) tendency for triggering side effects, such as unwanted sensory and/or motor responses. Such low amplitude signals can also reduce the power required by the implanted pulse generator, and can therefore extend the battery life and the associated time between recharging and/or replacing the battery.

Yet another expected benefit of providing therapy in accordance with the foregoing parameters is that the practitioner need not implant the lead with the same level of precision as is typically required for standard SCS lead placement. For example, while the foregoing results were identified for patients having two leads (one positioned on either side of the spinal cord midline), it is expected that patients will receive the same or generally similar pain relief with only a single lead placed at the midline. Accordingly, the practitioner may need to implant only one lead, rather than two. It is still further expected that the patient may receive pain relief on one side of the body when the lead is positioned offset from the spinal cord midline in the opposite direction. Thus, even if the patient has bilateral pain, e.g., with pain worse on one side than the other, the patient's pain can be addressed with a single implanted lead. Still further, it is expected that the lead position can vary laterally from the anatomical and/or physiological spinal cord midline to a position 3-5 mm. away from the spinal cord midline (e.g., out to the dorsal root entry zone or DREZ). The foregoing identifiers of the midline may differ, but the expectation is that the foregoing range is effective for both anatomical and physiological identifications of the midline, e.g., as a result of the robust nature of the present therapy. Yet further, it is expected that the lead (or more particularly, the active contact or contacts on the lead) can be positioned at any of a variety of axial locations in a range of about T9-T12 in one embodiment, and a range of one to two vertebral bodies within T9-T12 in another embodiment, while still providing effective treatment. Accordingly, the practitioner's selected implant site need not be identified or located as precisely as it is for standard SCS procedures (axially and/or laterally), while still producing significant patient benefits. In particular, the practitioner can locate the active contacts within the foregoing ranges without adjusting the contact positions in an effort to increase treatment efficacy and/or patient comfort. In addition, in particular embodiments, contacts at the foregoing locations can be the only active contacts delivering therapy to the patient. The foregoing features, alone or in combination, can reduce the amount of time required to implant the lead, and can give the practitioner greater flexibility when implanting the lead. For example, if the patient has scar tissue or another impediment at a preferred implant site, the practitioner can locate the lead elsewhere and still obtain beneficial results.

Still another expected benefit, which can result from the foregoing observed insensitivities to lead placement and signal amplitude, is that the need for conducting a mapping procedure at the time the lead is implanted may be significantly reduced or eliminated. This is an advantage for both the patient and the practitioner because it reduces the amount of time and effort required to establish an effective therapy regimen. In particular, standard SCS therapy typically requires that the practitioner adjust the position of the lead and the amplitude of the signals delivered by the lead, while the patient is in the operating room reporting whether or not pain reduction is achieved. Because the presently disclosed techniques are relatively insensitive to lead position and amplitude, the mapping process can be eliminated entirely. Instead, the practitioner can place the lead at a selected vertebral location (e.g., about T9-T12) and apply the signal at a pre-selected amplitude (e.g., 1 to 2 mA), with a significantly reduced or eliminated trial-and-error optimization process (for a contact selection and/or amplitude selection), and then release the patient. In addition to or in lieu of the foregoing effect, the practitioner can, in at least some embodiments, provide effective therapy to the patient with a simple bipole arrangement of electrodes, as opposed to a tripole or other more complex arrangement that is used in existing systems to steer or otherwise direct therapeutic signals. In light of the foregoing effect(s), it is expected that the time required to complete a patient lead implant procedure and select signal delivery parameters can be reduced by a factor of two or more, in particular embodiments. As a result, the practitioner can treat more patients per day, and the patients can more quickly engage in activities without pain.

The foregoing effect(s) can extend not only to the mapping procedure conducted at the practitioner's facility, but also to the subsequent trial period. In particular, patients receiving standard SCS treatment typically spend a week after receiving a lead implant during which they adjust the amplitude applied to the lead in an attempt to establish suitable amplitudes for any of a variety of patient positions and patient activities. Because embodiments of the presently disclosed therapy are relatively insensitive to patient position and activity level, the need for this trial and error period can be reduced or eliminated.

Still another expected benefit associated with embodiments of the presently disclosed treatment is that the treatment may be less susceptible to patient habituation. In particular, it is expected that in at least some cases, the high frequency signal applied to the patient can produce an asynchronous neural response, as is disclosed in co-pending U.S. application Ser. No. 12/362,244, previously incorporated herein by reference. The asynchronous response may be less likely to produce habituation than a synchronous response, which can result from lower frequency modulation.

Yet another feature of embodiments of the foregoing therapy is that the therapy can be applied without distinguishing between anodic contacts and cathodic contacts. As described in greater detail in U.S. application Ser. No. 12/765,790 (previously incorporated herein by reference), this feature can simplify the process of establishing a therapy regimen for the patient. In addition, due to the high frequency of the waveform, the adjacent tissue may perceive the waveform as a pseudo steady state signal. As a result of either or both of the foregoing effects, tissue adjacent both electrodes may be beneficially affected. This is unlike standard SCS waveforms for which one electrode is consistently cathodic and another is consistently anodic.

In any of the foregoing embodiments, aspects of the therapy provided to the patient may be varied within or outside the parameters used during the clinical testing described above, while still obtaining beneficial results for patients suffering from chronic low back pain. For example, the location of the lead body (and in particular, the lead body electrodes or contacts) can be varied over the significant lateral and/or axial ranges described above. Other characteristics of the applied signal can also be varied. For example, as described above, the signal can be delivered at a frequency of from about 1.5 kHz to about 100 kHz, and in particular embodiments, from about 1.5 kHz to about 50 kHz. In more particular embodiments, the signal can be provided at frequencies of from about 3 kHz to about 20 kHz, or from about 3 kHz to about 15 kHz, or from about 5 kHz to about 15 kHz, or from about 3 kHz to about 10 kHz. The amplitude of the signal can range from about 0.1 mA to about 20 mA in a particular embodiment, and in further particular embodiments, can range from about 0.5 mA to about 10 mA, or about 0.5 mA to about 4 mA, or about 0.5 mA to about 2.5 mA. The amplitude of the applied signal can be ramped up and/or down. In particular embodiments, the amplitude can be increased or set at an initial level to establish a therapeutic effect, and then reduced to a lower level to save power without forsaking efficacy, as is disclosed in pending U.S. application Ser. No. 12/264,836, filed Nov. 4, 2008 and incorporated herein by reference. In particular embodiments, the signal amplitude refers to the electrical current level, e.g., for current-controlled systems. In other embodiments, the signal amplitude can refer to the electrical voltage level, e.g., for voltage-controlled systems. The pulse width (e.g., for just the cathodic phase of the pulses) can vary from about 10 microseconds to about 333 microseconds. In further particular embodiments, the pulse width can range from about 25 microseconds to about 166 microseconds, or from about 33 microseconds to about 100 microseconds, or from about 50 microseconds to about 166 microseconds. The specific values selected for the foregoing parameters may vary from patient to patient and/or from indication to indication and/or on the basis of the selected vertebral location. In addition, the methodology may make use of other parameters, in addition to or in lieu of those described above, to monitor and/or control patient therapy. For example, in cases for which the pulse generator includes a constant voltage arrangement rather than a constant current arrangement, the current values described above may be replaced with corresponding voltage values.

In at least some embodiments, it is expected that the foregoing amplitudes will be suprathreshold. It is also expected that, in at least some embodiments, the neural response to the foregoing signals will be asynchronous, as described above. Accordingly, the frequency of the signal can be selected to be higher (e.g., between two and ten times higher) than the refractory period of the target neurons at the patient's spinal cord, which in at least some embodiments is expected to produce an asynchronous response.

Patients can receive multiple signals in accordance with still further embodiments of the disclosure. For example, patients can receive two or more signals, each with different signal delivery parameters. In one particular example, the signals are interleaved with each other. For instance, the patient can receive 5 kHz pulses interleaved with 10 kHz pulses. In other embodiments, patients can receive sequential "packets" of pulses at different frequencies, with each packet having a duration of less than one second, several seconds, several minutes, or longer depending upon the particular patient and indication.

In still further embodiments, the duty cycle may be varied from the 50%-100% range of values described above, as can the lengths of the on/off periods. For example, the duty cycle can be reduced to 25%. In some embodiments, it has been observed that patients can have therapeutic effects (e.g., pain reduction) that persist for significant periods after the modulation has been halted. In particular examples, the beneficial effects can persist for 10-20 minutes in some cases, and up to an hour in others and up to days or more in still further cases. Accordingly, the simulator can be programmed to halt modulation for periods of up to an hour, with appropriate allowances for the time necessary to re-start the beneficial effects. This arrangement can significantly reduce system power consumption, compared to systems with higher duty cycles, and compared to systems that have shorter on/off periods.

5.0 Representative Lead Configurations

Figure 9:
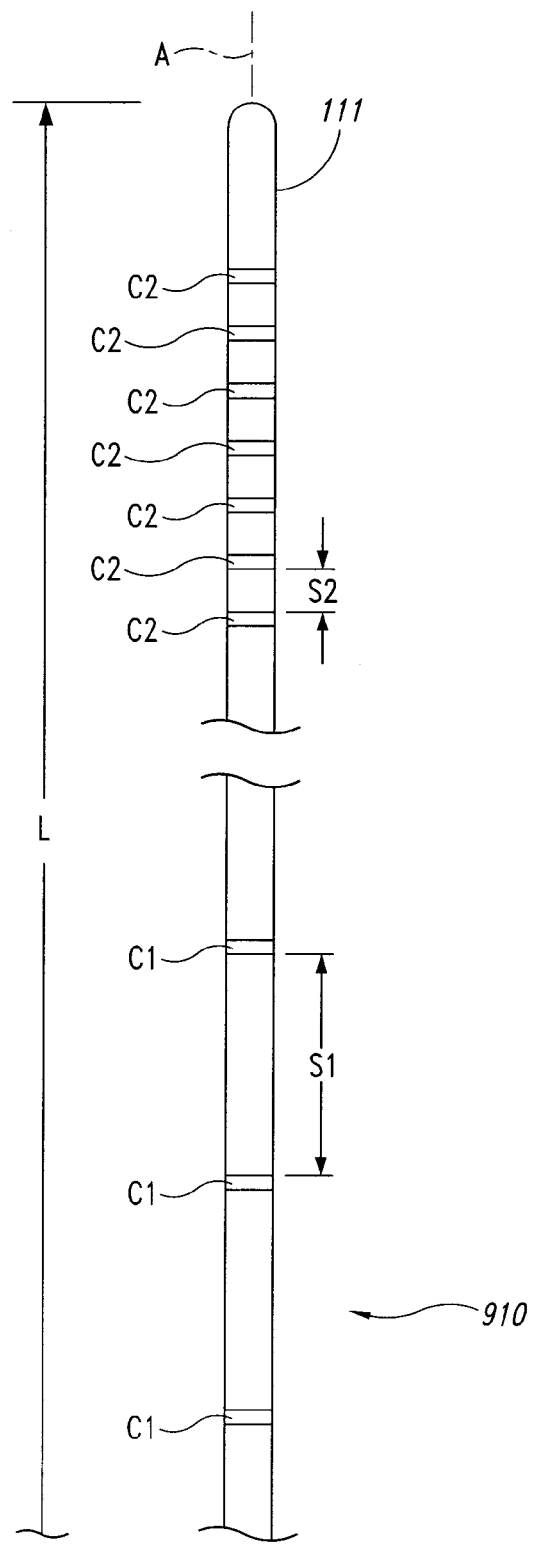
FIG. 9 is a partially schematic illustration of a lead body configured in accordance with an embodiment of the disclosure.

FIG. 9 is a partially schematic illustration of a lead 910 having first and second contacts C1, C2 positioned to deliver modulation signals in accordance with particular embodiments of the disclosure. The contacts are accordingly positioned to contact the patient's tissue when implanted. The lead 910 can include at least two first contacts C1 and at least two second contacts C2 to support bipolar modulation signals via each contact grouping. In one aspect of this embodiment, the lead 910 can be elongated along a major or lead axis A, with the contacts C1, C2 spaced equally from the major axis A. In general, the term elongated refers to a lead or other signal delivery element having a length (e.g., along the spinal cord) greater than its width. The lead 910 can have an overall length L (over which active contacts are positioned) that is longer than that of typical leads. In particular, the length L can be sufficient to position first contacts C1 at one or more vertebral locations (including associated neural populations), and position the second contacts C2 at another vertebral location (including associated neural populations) that is spaced apart from the first and that is superior the first. For example, the first contacts C1 may be positioned at vertebral levels T9-T12 to treat low back pain, and the second contacts C2 may be positioned at superior vertebral locations (e.g., cervical locations) to treat arm pain. Representative lead lengths are from about 30 cm to about 150 cm, and in particular embodiments, from about 40 cm to about 50 cm. Pulses may be applied to both groups of contacts in accordance with several different arrangements. For example pulses provided to one group may be interleaved with pulses applied to the other, or the same signal may be rapidly switched from one group to the other. In other embodiments, the signals applied to individual contacts, pairs of contacts, and/or contacts in different groups may be multiplexed in other manners. In any of these embodiments, each of the contacts C1, C2 can have an appropriately selected surface area, e.g., in the range of from about 3 $mm^2$ to about 25 $mm^2$, and in particular embodiments, from about 8 $mm^2$ to about 15 $mm^2$. Individual contacts on a given lead can have different surface area values, within the foregoing ranges, than neighboring or other contacts of the lead, with values selected depending upon features including the vertebral location of the individual contact.

Another aspect of an embodiment of the lead 910 shown in FIG. 9 is that the first contacts C1 can have a significantly wider spacing than is typically associated with standard SCS contacts. For example, the first contacts C1 can be spaced apart (e.g., closest edge to closest edge) by a first distance S1 that is greater than a corresponding second distance S2 between immediately neighboring second contacts C2. In a representative embodiment, the first distance S1 can range from about 3 mm up to a distance that corresponds to one-half of a vertebral body, one vertebral body, or two vertebral bodies (e.g., about 16 mm, 32 mm, or 64 mm, respectively). In another particular embodiment, the first distance S1 can be from about 5 mm to about 15 mm. This increased spacing can reduce the complexity of the lead 910, and can still provide effective treatment to the patient because, as discussed above, the effectiveness of the presently disclosed therapy is relatively insensitive to the axial location of the signal delivery contacts. The second contacts C2 can have a similar wide spacing when used to apply high frequency modulation in accordance with the presently disclosed methodologies. However, in another embodiment, different portions of the lead 910 can have contacts that are spaced apart by different distances. For example, if the patient receives high frequency pain suppression treatment via the first contacts C1 at a first vertebral location, the patient can optionally receive low frequency (e.g., 1500 Hz or less, or 1200 Hz or less), paresthesia-inducing signals at the second vertebral location via the second contacts C2 that are spaced apart by a distance S2. The distance S2 can be smaller than the distance S1 and, in particular embodiments, can be typical of contact spacings for standard SCS treatment (e.g., 4 mm spacings), as these contacts may be used for providing such treatment. Accordingly, the first contacts C1 can deliver modulation in accordance with different signal delivery parameters than those associated with the second contacts C2. In still further embodiments, the inferior first contacts C1 can have the close spacing S2, and the superior second contacts C2 can have the wide spacing S1, depending upon patient indications and/or preferences. In still further embodiments, as noted above, contacts at both the inferior and superior locations can have the wide spacing, e.g., to support high frequency modulation at multiple locations along the spinal cord. In other embodiments, the lead 910 can include other arrangements of different contact spacings, depending upon the particular patient and indication. For example, the widths of the second contacts C2 (and/or the first contacts C1) can be a greater fraction of the spacing between neighboring contacts than is represented schematically in FIG. 9. The distance S1 between neighboring first contacts C1 can be less than an entire vertebral body (e.g., 5 mm or 16 mm) or greater than one vertebral body while still achieving benefits associated with increased spacing, e.g., reduced complexity. The lead 910 can have all contacts spaced equally (e.g., by up to about two vertebral bodies), or the contacts can have different spacings, as described above. Two or more first contacts C1 can apply modulation at one vertebral level (e.g., T9) while two or more additional first contacts C1 can provide modulation at the same or a different frequency at a different vertebral level (e.g., T10).

In some cases, it may be desirable to adjust the distance between the inferior contacts C1 and the superior contacts C2. For example, the lead 910 can have a coil arrangement (like a telephone cord) or other length-adjusting feature that allows the practitioner to selectively vary the distance between the sets of contacts. In a particular aspect of this arrangement, the coiled portion of the lead can be located between the first contacts C1 and the second contacts C2. For example, in an embodiment shown in FIG. 10A, the lead 910 can include a proximal portion 910a carrying the first contacts C1, a distal portion 910c carrying the second contacts C2, and an intermediate portion 910b having a pre-shaped, variable-length strain relief feature, for example, a sinusoidally-shaped or a helically-shaped feature. The lead 910 also includes a stylet channel or lumen 915 extending through the lead 910 from the proximal portion 910a to the distal portion 910c.

Figure 10A:
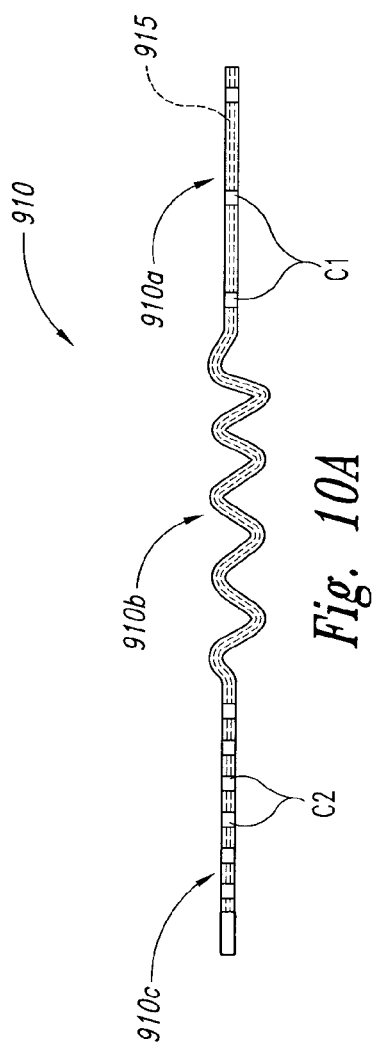
FIGS. 10A-10C are partially schematic illustrations of extendible leads configured in accordance with several embodiments of the disclosure.
Figure 10B:
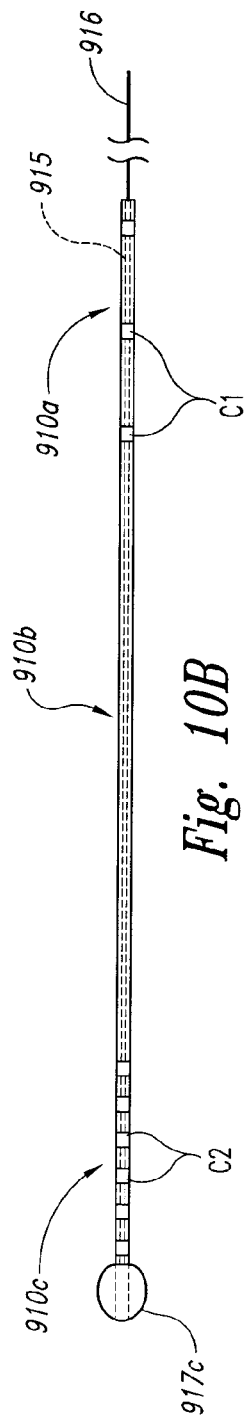

Referring next to FIG. 10B, the practitioner inserts a stylet 916 into the stylet lumen 915, which straightens the lead 910 for implantation. The practitioner then inserts the lead 910 into the patient, via the stylet 916, until the distal portion 910c and the associated second contacts C2 are at the desired location. The practitioner then secures the distal portion 910c relative to the patient with a distal lead device 917c. The distal lead device 917c can include any of a variety of suitable remotely deployable structures for securing the lead, including, but not limited to an expandable balloon.

Figure 10C:
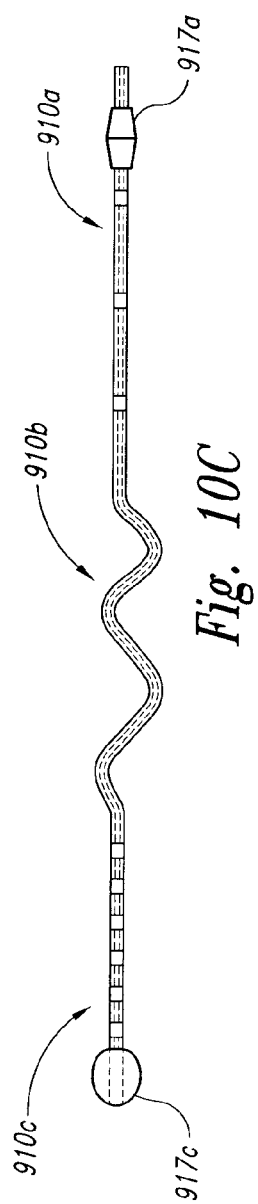
Figure 12:
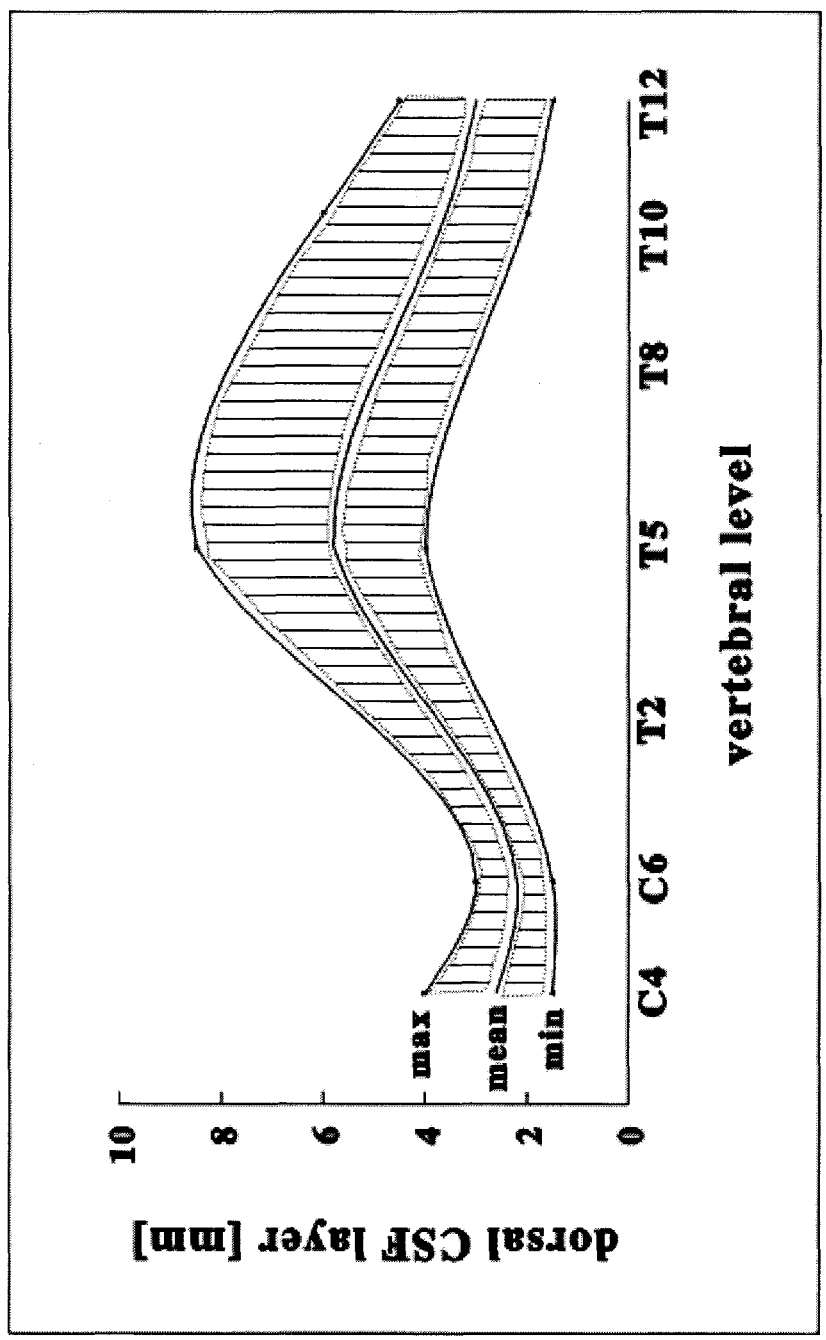
FIG. 12 is a graph illustrating dorsal column CSF layer thickness as a function of vertebral level for a representative human population.

Referring next to FIG. 10C, the practitioner can partially or completely remove the stylet 916 and allow the properties of the lead 910 (e.g., the natural tendency of the intermediate portion 910b to assume its initial shape) to draw the proximal portion 910a toward the distal portion 910c. When the proximal portion 910a has the desired spacing relative to the distal portion 910c, the practitioner can secure the proximal portion 910a relative to the patient with a proximal lead device 917a (e.g., a suture or other lead anchor). In this manner, the practitioner can select an appropriate spacing between the first contacts C1 at the proximal portion 910a and the second contacts C2 at distal portion 910c that provides effective treatment at multiple patient locations along the spine.

FIG. 11A is an enlarged view of the proximal portion 910a of the lead 910, illustrating an internal arrangement in accordance with a particular embodiment of the disclosure. FIG. 11B is a cross-sectional view of the lead 910 taken substantially along line 11B-11B of FIG. 11A. Referring now to FIG. 11B, the lead 910 can include multiple conductors 921 arranged within an outer insulation element 918, for example, a plastic sleeve. In a particular embodiment, the conductors 921 can include a central conductor 921a. In another embodiment, the central conductor 921a can be eliminated and replaced with the stylet lumen 915 described above. In any of these embodiments, each individual conductor 921 can include multiple conductor strands 919 (e.g., a multifilar arrangement) surrounded by an individual conductor insulation element 920. During manufacture, selected portions of the outer insulation 918 and the individual conductor insulation elements 920 can be removed, thus exposing individual conductors 921 at selected positions along the length of the lead 910. These exposed portions can themselves function as contacts, and accordingly can provide modulation to the patient. In another embodiment, ring (or cylinder) contacts are attached to the exposed portions, e.g., by crimping or welding. The manufacturer can customize the lead 910 by spacing the removed sections of the outer insulation element 918 and the conductor insulation elements 920 in a particular manner. For example, the manufacturer can use a stencil or other arrangement to guide the removal process, which can include, but is not limited to, an ablative process. This arrangement allows the same overall configuration of the lead 910 to be used for a variety of applications and patients without major changes. In another aspect of this embodiment, each of the conductors 921 can extend parallel to the others along the major axis of the lead 910 within the outer insulation 918, as opposed to a braided or coiled arrangement. In addition, each of the conductor strands 919 of an individual conductor element 920 can extend parallel to its neighbors, also without spiraling. It is expected that these features, alone or in combination, will increase the flexibility of the overall lead 910, allowing it to be inserted with a greater level of versatility and/or into a greater variety of patient anatomies then conventional leads.

FIG. 11C is a partially schematic, enlarged illustration of the proximal portion 910a shown in FIG. 11A. One expected advantage of the multifilar cable described above with reference to FIG. 11B is that the impedance of each of the conductors 921 can be reduced when compared to conventional coil conductors. As a result, the diameter of the conductors 921 can be reduced and the overall diameter of the lead 910 can also be reduced. One result of advantageously reducing the lead diameter is that the contacts C1 may have a greater length in order to provide the required surface area needed for effective modulation. If the contacts C1 are formed from exposed portions of the conductors 921, this is not expected to present an issue. If the contacts C1 are ring or cylindrical contacts, then in particular embodiments, the length of the contact may become so great that it inhibits the practitioner's ability to readily maneuver the lead 910 during patient insertion. One approach to addressing this potential issue is to divide a particular contact C1 into multiple sub-contacts, shown in FIG. 11C as six sub-contacts C1a-C1f. In this embodiment, each of the individual sub-contacts C1a-C1f can be connected to the same conductor 921 shown in FIG. 11B. Accordingly, the group of sub-contacts connected to a given conductor 921 can operate essentially as one long contact, without inhibiting the flexibility of the lead 910.

As noted above, one feature of the foregoing arrangements is that they can be easy to design and manufacture. For example, the manufacturer can use different stencils to provide different contact spacings, depending upon specific patient applications. In addition to or in lieu of the foregoing effect, the foregoing arrangement can provide for greater maneuverability and facilitate the implantation process by eliminating ring electrodes and/or other rigid contacts, or dividing the contacts into subcontacts. In other embodiments, other arrangements can be used to provide contact flexibility. For example, the contacts can be formed from a conductive silicone, e.g., silicone impregnated with a suitable loading of conductive material, such as platinum, iridium or another noble metal.

Yet another feature of an embodiment of the lead shown in FIG. 9 is that a patient can receive effective therapy with just a single bipolar pair of active contacts. If more than one pair of contacts is active, each pair of contacts can receive the identical waveform, so that active contacts can be shorted to each other. In another embodiment, the implanted pulse generator (not visible in FIG. 9) can serve as a return electrode. For example, the pulse generator can include a housing that serves as the return electrode, or the pulse generator can otherwise carry a return electrode that has a fixed position relative to the pulse generator. Accordingly, the modulation provided by the active contacts can be unipolar modulation, as opposed to the more typical bipolar stimulation associated with standard SCS treatments.

6.0 Representative Programmer Configurations

The robust characteristics of the presently disclosed therapy techniques may enable other aspects of the overall system described above with reference to FIGS. 1A-B to be simplified. For example, the patient remote and the physician programmer can be simplified significantly because the need to change signal delivery parameters can be reduced significantly or eliminated entirely. In particular, it is expected that in certain embodiments, once the lead is implanted, the patient can receive effective therapy while assuming a wide range of positions and engaging in a wide range of activities, without having to change the signal amplitude or other signal delivery parameters. As a result, the patient remote need not include any programming functions, but can instead include a simple on/off function (e.g., an on/off button or switch), as described further in U.S. application Ser. No. 12/765,790 (previously incorporated herein by reference). The patient remote may also include an indicator (e.g., a light) that identifies when the pulse generator is active. This feature may be particularly useful in connection with the presently disclosed therapies because the patient will typically not feel paresthesia, unless the system is configured and programmed to deliberately produce paresthesia in addition to the therapy signal. In particular embodiments, the physician programmer can be simplified in a similar manner, though in some cases, it may be desirable to maintain at least some level of programming ability at the physician programmer. Such a capability can allow the physician to select different contacts and/or other signal delivery parameters in the rare instances when the lead migrates or when the patient undergoes physiological changes (e.g., scarring) or lifestyle changes (e.g., new activities) that are so significant they require a change in the active contact(s) and/or other signal delivery parameters.

7.0 Representative Modulation Locations and Indications

Many of the embodiments described above were described in the context of treating chronic, neuropathic low back pain with modulation signals applied to the lower thoracic vertebrae (T9-T12). In other embodiments, modulation signals having parameters (e.g., frequency, pulse width, amplitude, and/or duty cycle) generally similar to those described above can be applied to other patient locations to address other indications. For example, while the foregoing methodologies included applying modulation at lateral locations ranging from the spinal cord midline to the DREZ, in other embodiments, the modulation may be applied to the foramen region, laterally outward from the DREZ. In other embodiments, the modulation may be applied to other spinal levels of the patient. For example, modulation may be applied to the sacral region and more particularly, the "horse tail" region at which the sacral nerves enter the sacrum. Urinary incontinence and fecal incontinence represent example indications that are expected to be treatable with modulation applied at this location. In other embodiments, the modulation may be applied to other thoracic vertebrae. For example, modulation may be applied to thoracic vertebrae above T9. In a particular embodiment, modulation may be applied to the T3-T6 region to treat angina. Modulation can be applied to high thoracic vertebrae to treat pain associated with shingles. For example, modulation signals can be applied at vertebral levels of from about T3 to about T7 to address shingles with chest wall manifestations. In other embodiments, the modulation signals may be applied at higher vertebral levels, e.g., at cervical levels to address shingles affecting the trigeminal nerve (indicated later with reference to Table 1). Modulation may be applied to the cervical vertebrae to address chronic regional pain syndrome and/or total body pain, and may be used to replace neck surgery. Suitable cervical locations include vertebral levels C3-C7, inclusive. In other embodiments, modulation may be applied to the occipital nerves, for example, to address migraine headaches. Representative embodiments are described further below.

7.1 Headache Pain Relief

In particular embodiments, modulation signals in accordance with the parameters described above (e.g., frequencies of from about 1.5 kHz to about 100 kHz, or from about 1.5 kHz to about 50 kHz., or from about 3 kHz to about 20 kHz, or from about 3 kHz to about 15 kHz, or from about 5 kHz to about 15 kHz, or from about 3 kHz to about 10 kHz) are applied epidurally to the spine at high cervical locations to achieve patient headache pain relief. For example, the modulation signals can be applied at the C1, C2 and/or C3 vertebral levels. In at least some of these embodiments, the signals can affect the trigeminal nerve, the caudate nucleus and/or the pons. In a particular embodiment, the modulation signal was applied at the mid-high C2 level, resulting in patient relief from migraine pain. It is expected that the modulation signal at this location affected the C2 or C2/C3 spinal nerves. In other embodiments, the effect of the modulation signal may be indirect, e.g., a synapse away from the synapse nearest the modulation location.

The foregoing modulation therapy can have particular applicability to cervicogenic headaches, for example, in the occipital and/or temporal areas. Cervicogenic headaches can caused by whiplash injuries and/or other traumas and/or disorders of the neck. In other embodiments, the foregoing techniques can be used to address other types of secondary headache pain, for example, headache pain caused by tumors. In still further embodiments, the foregoing techniques can be used to address primary headache pain, for example, tension headaches, cluster headaches and/or migraine headaches, as in the example described above. In general, modulation signals can be applied from C1-C5, inclusive, to treat migraine/headache pain and/or any other type of cephalic or cevicogenic pain. In particular embodiments, modulation signals are applied at one or more locations from about C1 to about C4, or about C2 to about C4, to address migraine, headache, and/or facial pain.

7.2 Total Body Pain Relief

In a particular embodiment, modulation signals are applied epidurally to the spinal cord at the cervical vertebrae (e.g., C3-C7 or C3-C6) to obtain total body pain relief. As used herein, total body pain relief refers to relief of non-cephalic pain in the trunk and in some cases the limbs as well. This is distinct from the four-limb paresthesia occasionally reported with standard SCS (e.g., low frequency) stimulation of the spinal cord at cervical locations. Instead, the modulation signals applied in accordance with the present technology are applied epidurally at frequencies of from about 1.5 kHz to about 100 kHz, or from about 1.5 kHz to about 50 kHz., or from about 3 kHz to about 20 kHz, or from about 3 kHz to about 15 kHz, or from about 5 kHz to about 15 kHz, or from about 3 kHz to about 10 kHz. In a manner generally similar to that discussed above, it is expected that modulation signals applied to the dorsal region of the spinal cord at frequencies within the foregoing ranges will provide pain relief without paresthesia, without motor capture and without interference with other sensory signals. In addition, the modulation signals can be applied at relatively low amplitudes that do not trigger unwanted side effects. This again is unlike conventional spinal cord stimulation techniques which are performed at low frequencies (e.g., generally less than 200 Hz), and which are expected to require amplitudes at levels high enough to cause patient pain before achieving total body pain relief. As discussed above, the high frequency modulation signals can be less likely to produce patient pain (and/or other undesirable side effects). Accordingly, the practitioner can have greater flexibility in selecting the modulation site (e.g., in selecting the lateral and/or axial location for the signal delivery device), which allows the practitioner to produce wider ranging benefits without incurring the undesirable side effects.

The following example is taken from clinical trial data associated with a patient receiving neural modulation therapy in accordance with a particular example of the technology disclosed herein. The patient suffered for years from neck pain, leg pain and back pain. Approximately seven years prior to receiving neural modulation therapy in accordance with the present technology, the patient received a conventional implanted SCS system, with two leads in the neck and two leads at approximately vertebral level T9. All four leads were attached to a single pulse generator which the patient controlled with an external control device. One of the neck leads repeatedly migrated from the patient's neck to the patient's jaw. After the neck lead was repositioned unsuccessfully twice, it was left in place at the patient's jaw. The device worked reasonably well for about four years, although the patient disliked the sensation of paresthesia. Then the device stopped functioning, and had been inactive for approximately two years prior to the patient receiving the presently disclosed therapy.

Figure 13:
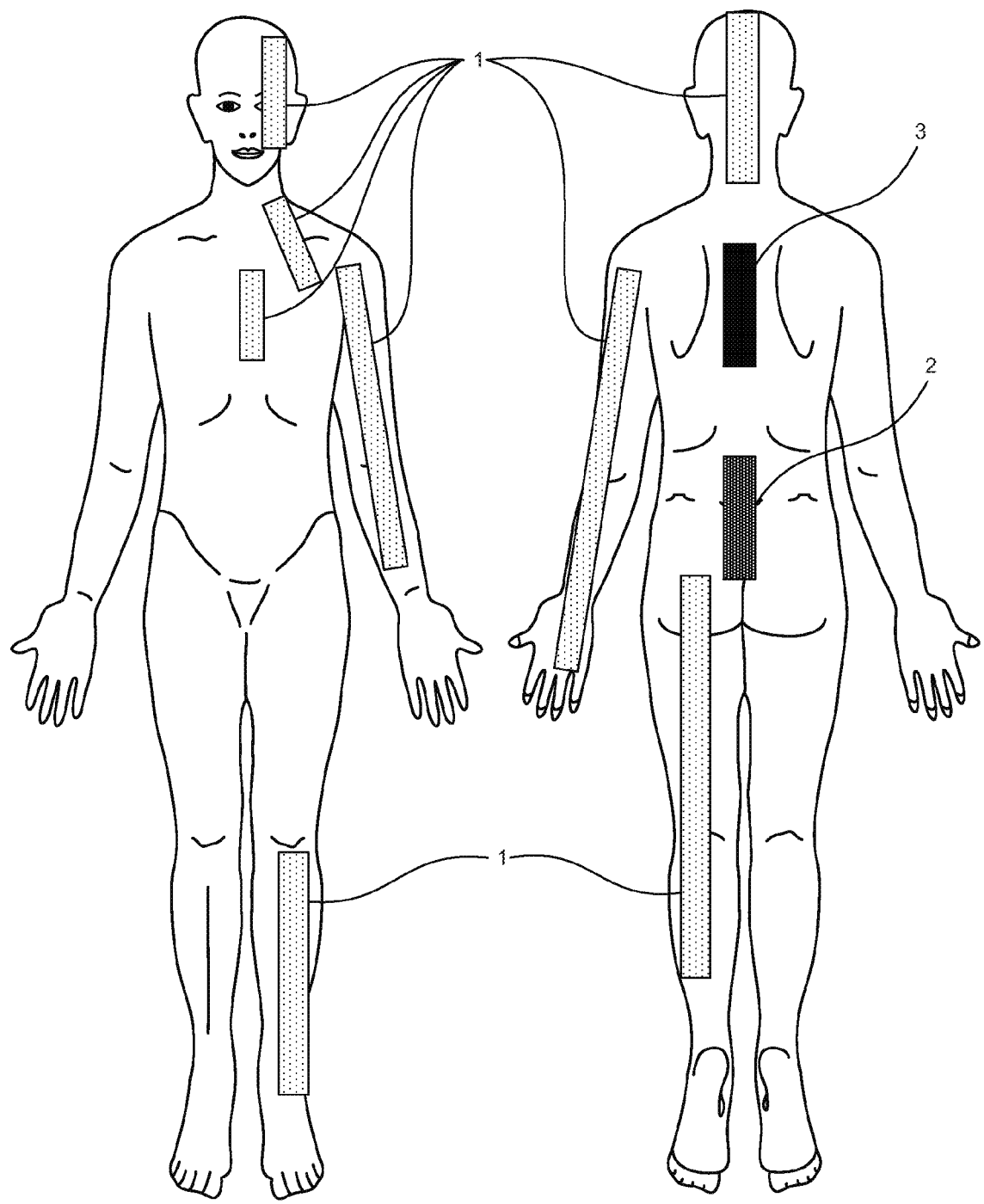
FIG. 13 is a pain map illustrating pain locations for a patient prior to receiving neural modulation therapy in accordance with an embodiment of the present technology
Figure 14:
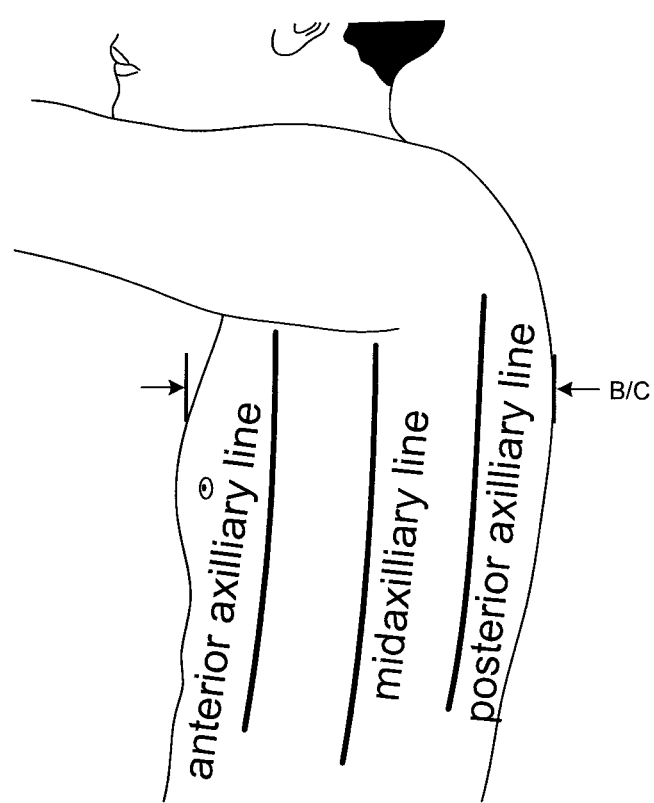
FIG. 14 is an illustration of a patient identifying the midaxillary line.

In addition to the conventional SCS therapy, the patient received drug therapy for 7-8 years. The drugs were delivered to the patient's spinal cord at a vertebral level of approximately T9. Two years prior to receiving the presently disclosed therapy, the patient also received standard SCS leads implanted subcutaneously at the head to control head pain. At the time the patient received the presently disclosed therapy, the head leads were still active, though not particularly effective, and the patient continued to dislike the paresthesia sensations. FIG. 13 illustrates a map identifying the locations at which the patient felt pain, along with an indication of the relative severity of the pain, prior to receiving neural modulation therapy in accordance with the present technology. Areas identified with numeral 2 were more painful than areas identified with numeral 1, and areas identified with numeral 3 were more painful than areas identified with numeral 2.

In accordance with the presently disclosed technology, the patient initially received a lead implanted epidurally with contacts at the C3-C4 vertebral level. Neural modulation signals were applied to the lead at a frequency of 10 kHz and at a controllable amplitude. At a current amplitude of 0.7 mA, the patient reported an entirely pain-free day. During this day, the patient reported no pain at any of the locations identified in FIG. 13, and reported feeling much better.

After receiving the implanted lead with active contacts at the C3-C4 vertebral level, and associated neural modulation therapy, the patient's pain medication was reduced by 28%. The patient subsequently experienced an associated increase in pain. Due to the nature of this particular trial, a new lead with contacts at T9-T10 was activated at 10 kHz and 3 mA to address the patient's pain. Accordingly, the patient received neural modulation at a frequency of 10 kHz at both the C3-C4 vertebral level and the T9-T10 vertebral level. In particular, the patient received therapy at the C3-C4 location, alternated on a one-second/one-second basis with therapy at the T9-T10 location. The patient thereafter was pain-free, consistent with the patient's reported condition when receiving C3-C4 modulation at 0.7 mA alone. The patient continued to experience no paresthesia. Based at least in part on this experience, and at the time of filing the present application, it is expected that the full extent of the pain relief obtained by the patient on the first day will again be realized even after the T9-T10 modulation ceases, for this patient and/or patients with similar indications. This expectation is consistent with other data indicating total pain relief in patients receiving the presently disclosed therapy at particular locations, e.g., epidural cervical locations.

In another example, a patient experienced high and low back pain, as well as leg pain. Prior to receiving therapy in accordance with the presently disclosed technology, the patient reported a pain level of 8 (on a scale of 0-10, 10 being the worst pain) at the upper and lower back, and 4 at the leg. The patient received neural modulation therapy via a 10 kHz signal delivered from contacts placed at the C6-C7 vertebral levels. The patient reported a reduction in the high and low back pain from 8 to 2, and in the leg pain from 4 to 0. At the conclusion of the trial, the patient reported a return of the pain beginning at about 2 hours post-trial.

Based on the foregoing results, it is believed that embodiments of the presently disclosed therapy can address pain over a wide range of dermatomes via active contacts located at cervical vertebral levels. This approach can be used to address neck pain, high back pain (e.g., pain from about the base of the neck to about the caudal edge of the scapulas, mid back pain (e.g., pain from about the bottom of the scapulas to about the waist), low back pain (e.g., from about the waist to the line formed by the hip joints) and/or leg pain (e.g., below the hip joints), in addition to or in lieu of addressing headache pain and/or total body pain. This degree of pain relief is not believed to be available with existing standard SCS systems.

In still further embodiments, total body pain can be addressed via modulation at somewhat more caudal vertebral levels. For example, the modulation signals can be delivered at the T2 vertebral level to address total body pain. The practitioner can also select modulation at the T2 vertebral level to address fibromyalgia, in addition to or in lieu of addressing total body pain with such modulation.

One particular difficulty with standard SCS systems is the ability to address mid-back pain, e.g., pain at approximately the T4-T5 dermatomes. The general experience is that a standard SCS lead implanted at or near these dermatomes will trigger adverse pain effects at the dorsal roots before triggering beneficial effects at the dorsal column. One possible reason for this effect is that at or around the T4-T5 dermatomes, the shape of the epidural space becomes more elongated in the dorsal/ventral direction. Accordingly, a lead placed epidurally is forced to a position further away from the dorsal column than from the dorsal roots. Delivering standard SCS therapy from this location will then have an adverse effect on the dorsal roots. However, it is expected that the presently disclosed therapy will have a beneficial effect without creating the adverse effects described above.

Another difficulty associated with conventional methods for delivering neural modulation to the cervical and high/mid-back locations relates to the implantation site for the IPG. If the IPG is implanted just above the buttock (as shown in FIG. 1A), the practitioner must either (1) tunnel the lead though nearly the entire length of the spinal canal, or (2) tunnel the lead subcutaneously up to a relatively high thoracic vertebra, and then thread the lead into the spinal canal and up to the desired vertebral location. A problem with the first method is that it can be difficult to successfully position the lead when tunneling over such a long distance within the spinal canal. A problem with the second method is that the practitioner must tunnel through the tough subcutaneous fibroid sheath which spans laterally across the back from the high thoracic region to the low thoracic region, and which can require a significant amount of force, and therefore can increase the likelihood for damage to the patient.

An embodiment of the present technology can address the foregoing drawbacks. In particular, the IPG can be implanted under the patient's armpit along the midaxillary line, shown in FIG. 14. The lead can be routed around the patient's side to the spinal canal at or close to the target vertebral level (1) without requiring a long tunneling procedure in the spinal canal and (2) without requiring the lead to traverse the fibroid sheath. Furthermore, by placing the IPG at or near the midaxillary line, the practitioner can avoid a placing the IPG at a subclavicular location. This is advantageous because it avoids the need to turn the patient over and redrape the patient during the implantation procedure. Instead, the practitioner can implant the IPG with the patient in the same (prone) position used to implant the lead, and can access the midaxillary location by opening the existing drape.

The particular location of the IPG for a midaxillary implant can vary depending on the physiology of the patient and/or the size of the IPG. In general, the IPG can be implanted directly on the midaxillary line, or offset from the midaxillery line (e.g., toward the chest or toward the back) in a manner that does not produce a visual bulge in the patient's skin. In particular embodiments, the offset distance is measured relative to a back/chest thickness B/C of the patient. The back/chest thickness can be measured between the musculature of the patient's chest (e.g., excluding mammary glands in female patients) and the musculature of the patient's back. In particular embodiments, the IPG can be implanted at a location within ±20% of the back/chest thickness B/C from the midaxillary line.

One characteristic associated with a midaxillary implant is that the IPG will typically need to be smaller than an IPG placed at the buttock. One way to achieve a smaller IPG size is to reduce the size of the battery. Typically, this will reduce the time between battery charging events, which is inconvenient for the patient. However, the presently disclosed technology can enable IPGs with smaller batteries. In particular, as discussed above, patients receiving the presently disclosed therapy have experienced pain relief that lasts for a significant period of time after the neural modulation signal has ceased. This is unlike the patient experience with standard SCS, which is that the pain returns immediately upon ceasing the SCS signal. Accordingly, the present therapy can be administered with significant "off" periods (e.g., by selecting an appropriate duty cycle). Duty cycling reduces the power required by the system, which in turn reduces the size of the battery required by the system, which in turn reduces the size of the IPG and improves the ability of the IPG to fit in a midaxillary (or other compact) implant site.

In at least some embodiments, it is expected that both headache pain relief and total body pain relief may result from modulating one or more of the patient's neural augmentation pathways (e.g., the post-synaptic dorsal column pathway), which are highly sensitive. In fact, the post-synaptic dorsal column pathway has historically been cut by surgeons so as to reduce patient pain. Rather than cutting the pathway, techniques in accordance with the present technology can include applying electrical signals to modify the transmission of pain signals along the pathway, thus reducing or inhibiting patient pain sensations. For example, the modulation signals described above can keep the target nerves in a refractory state to inhibit pain signal transmission, as disclosed in greater detail in pending U.S. application Ser. No. 12/362,244, previously incorporated herein by reference. Still further mechanisms of actions are disclosed in co-pending U.S. application Ser. No. 13/308,436, filed Nov. 30, 2011 and incorporated herein by reference.

In at least some cases, the beneficial results associated with modulating the spinal cord at the cervical vertebrae can be associated with the relatively thin layer of cerebral spinal fluid (CSF) at these vertebral levels. For example, FIG. 12 (based on information from Holsheimer and Barolat, "Spinal Geometry and Paresthesia Coverage in Spinal Cord Stimulation" (1998) "Neuromodulation" Vol. 1 No. 3:129-136) illustrates representative minimum, maximum and mean CSF layer thicknesses from vertebral levels C4 to T12. The reduced CSF layer thickness at the upper thoracic vertebra and lower cervical vertebrae can result in increased modulation signal efficacy and/or a reduced power level to obtain patient pain relief. Therapeutic efficacy requires targeting the appropriate nerve population, and so the effect of the reduced CSF layer thickness is expected to be realized in particular when addressing pain associated with nerves that enter the spinal column at or caudal to these vertebral levels.

The beneficial results described above may be due to the shape of the spinal cord at the cervical region, in addition to or in lieu of the CSF layer thickness in this region. In particular, the spinal cord has a more oblate cross-sectional shape in the cervical region. Accordingly, modulation signals applied at or near the dorsal midline have a reduced tendency to create unwanted effects at the laterally located spinal roots. In addition to or in lieu of the foregoing effect, the high frequency characteristics of signals applied in accordance with the present technology can improve therapeutic efficacy. For example, high frequency signals are expected in at least some embodiments to penetrate deeper into the spinal cord tissue than lower frequency signals at the same amplitude, e.g., due to capacitive coupling. The result in at least some embodiments is an increased therapeutic effect on smaller and/or deeper fibers.

7.3 Other Indications

In still further embodiments, modulation can be applied to patients having visceral pain, facial pain, pelvic pain, and/or peripheral vascular disease. Table 1 includes a listing of additional indications.

TABLE 1

| Indication | Modulation Target |
|---|---|
| A. Headache Pain Syndromes | C1-C5, e.g., C2-C3 |
| Herpes Zoster (shingles) - Trigeminal | |
| Migraine | (e.g., C4-C5) |
| Cluster | |
| Swimmer's | |
| Analgesic rebound | |
| Occipital neuralgia | |
| B. Pain Syndromes | C2-C4, e.g, C2-C3 |
| Trigeminal neuralgia | |
| Temporomandibular Joint Dysfunction | |
| Atypical Facial Pain | |
| Myofascial Pain Syndrome - Face | |
| Cancer Pain | |
| Hyoid Syndrome | |
| Reflex Sympathetic Dystrophy-Face | |
| C. Neck & Brachial Plexus Pain Syndromes | C2-C6, e.g., C3-C4 |
| Cervical Facet Syndrome | |
| Cervical Radiculopathy | |
| Fibromyalgia - Cervical Musculature | |
| Myofascial Pain Syndrome - Cervical Musculature | |
| Cervical Strain | |
| Cervicothoracic Interspinous Bursitis Syndrome | |
| Spinal Stenosis | |
| Brachial Plexopathy | |
| Pancoast's Syndrome | |
| Thoracic Outlet Syndrome | |
| D. Shoulder Pain Syndromes | C2-C6, e.g., C3-C5 |
| Arthritis Pain -Shoulder | |
| Acromio-clavicular Joint Pain | |
| Fibromyalgia - Shoulders | |
| Myofascial Pain Syndrome - Shoulders | |
| Subdeltoid Bursitis | |
| Bicipital Tendonitis | |
| Supraspinatus Syndrome | |
| Rotator Cuff Tear | |
| Deltoid Syndrome | |
| Teres Major Syndrome | |
| Scapulocostal Syndrome | |
| E. Elbow Pain Syndromes | C2-C6, e.g., C3-C5 |
| Arthritis Pain-Elbow | |
| Tennis Elbow | |
| Golfer's Elbow | |
| Anconeus Syndrome | |
| Supinator Syndrome | |
| Brachioradialis Syndrome | |
| Ulnar Nerve Entrapment At The Elbow | |
| Lateral Antebrachial Cutaneous Nerve Syndrome | |
| Olecranon Bursitis | |
| F. Other Upper Extremity Pain Syndromes | C2-C6,, e.g., C3-C5 |
| Fibromyalgia - Arms | |
| Myofascial Pain Syndrome | |
| Phantom Limb Pain | |
| G. Wrist Pain Syndromes | C2-C6, e.g., C3-C5 |
| Arthritis Pain - Wrist | |
| Carpal Tunnel Syndrome | |
| De Quervain's Tenosynovitis | |
| Arthritis Pain - Carpometacarpal Joints | |
| H. Hand Pain Syndromes | C2-C6, e.g., C3-C5 |
| Arthritis Pain - Fingers | |
| Trigger Thumb | |
| Trigger Finger | |
| Ganglion Cysts Of Wrist & Hand | |
| Sesamoiditis Of The Hand | |
| Plastic Bag Palsy | |
| Carpal Boss Syndrome | |
| Dupuytren's Contracture | |
| I. Chest Wall Pain Syndromes | T1-T12 |
| Costosternal Syndrome | |
| Manubriosternal Joint Pain | |
| Intercostal Neuralgia | |
| Diabetic Truncal Neuropathy | |
| Tietze's Syndrome | |
| Precordial Catch Syndrome | |
| Fractured Ribs | |
| Post-Thoracotomy Pain | |
| J. Thoracic Spine Pain Syndromes | T1-T12 |
| Acute Herpes Zoster - Thoracic Dematome | |
| Cancer Pain | |
| Costovertebral Arthritis Pain | |
| Postherpetic Neuralgia | |
| Spinal Stenosis | |
| Thoracic Vertebral Compression Fractures | |
| K. Abdominal & Groin Pain Syndromes | T6-T12 |
| Acute Pancreatitis | |
| Cancer Pain | |
| Chronic Pancreatitis | |
| Ilioinguinal Neuralgia | |
| Visceral Pain (peritoneum, stomach, duodenum, intestine, colon, liver, spleen, pancreas, kidney, adrenal gland, appendix, gall bladder) | |
| Post-vasectomy Pain Syndrome | |
| Genitofemoral Neuralgia | |

TABLE 1-continued

| Indication | Modulation Target |
|---|---|
| Interstitial Cystitis | |
| L. Lumbar Spine & Sacroiliac Joint Pain Syndromes | T8-T12 |
| Fibromyalgia - Lumbar Musculature | |
| Myofascial Pain Syndrome | |
| Lumbar Radiculopathy | |
| Latissimus Dorsi Muscle Syndrome | |
| Spinal Stenosis | |
| Arachnoiditis | |
| Sacroiliac Joint Pain | |
| M. Pelvic Pain Syndromes | T12-L5 |
| Osteitis Pubis | |
| Cancer Pain | |
| Gluteus Maximus Syndrome | |
| Visceral Pain (pelvis, coccyx, ovaries, fallopian tube, uterus, vulva, clitoris, perineum, urinary bladder, testicles, rectum) | |
| Piriformis Syndrome | |
| Ischiogluteal Bursitis | |
| Levator Ani Syndrome | |
| Coccydynia | |
| Interstitial Cystitis | |
| Vulvodynia | |
| N. Hip & Lower Extremity Pain Syndromes | T7-T12 |
| Fibromyalgia - Lower Extremity Musculature | |
| Myofascial Pain Syndrome - Lower Extremity Musculature | |
| Arthritis Pain - Hip | |
| Snapping Hip Syndrome | |
| Restless leg syndrome | |
| Iliopectinate Bursitis | |
| Ischial Bursitis | |
| Meralgia Paresthetica | |
| Phantom Limb Pain | (e.g., T7-T10) |
| Trochanteric Bursitis | |
| O. Knee Pain Syndromes | T8-T12 |
| Arthritis Pain - Knee | |
| Medial Collateral Ligament | |
| Jumper's Knee Syndrome | |
| Runner's Knee Syndrome | |
| Suprapatellar Bursitis | |
| Prepatellar Bursitis | |
| Superficial Infrapatellar Bursitis | |
| Deep Infrapatellar Bursitis | |
| Baker's Cyst | |
| Pes Anserine Bursitis | |
| P. Ankle Pain Syndromes | T8-T12 |
| Arthritis Pain - Ankle | |
| Arthritis Midtarsal Joints | |
| Deltoid Ligament Strain | |
| Anterior Tarsal Tunnel Syndrome | |
| Posterior Tarsal Tunnel Syndrome | |
| Achilles Tendonitis | |
| Q. Foot Pain Syndromes | T8-T12 |
| Arthritis - Toe Pain | |
| Bunion Pain | |
| Gout | |
| Morton's Neuroma | |
| Plantar Fascitis | |
| Calcaneal Spur Syndrome | |
| Mallet Toe Syndrome | |
| Hammer Toe Syndrome | |
| R. Whole Body Pain Syndromes | C2-C4 |
| Fybromyalgia | |
| Cancer Pain | |
| Chronic Regional Pain Syndrome - Multiple Limb | |
| Other syndromes with difficult anatomical targets | |

The vertebral levels identified in Table 1 and in at least some instances elsewhere in the present disclosure, apply generally to signal delivery devices placed at or near the spinal cord midline. For signal delivery devices placed off the midline, the affected dermatome(s) and indications may be at, or at least closer to, the vertebral level at which the signal delivery device is located. This effect is expected to be more pronounced at lower vertebral levels than at higher vertebral levels because at lower vertebral levels, nerves tend to extend further in a cephalad direction before entering the spinal cord and/or before attaining a position within the spinal cord that is close to the midline. For example, a signal delivery device placed at or near midline at the T2 vertebral level may address dermatomes below T6, while a signal delivery device placed off-midline at T2 may address dermatomes up and including T2. Off-midline signal delivery devices may also address more localized dermatomes. In the example above, an off-midline signal delivery device at T2 may address dermatomes only at or close to T2. This effect is expected to decrease at higher vertebral levels, and/or as a result of the high-frequency nature of the signals delivered in accordance with the present technology. Such signals are expected to produce a broader field than do standard SCS signals.

In one representative example identified in Table 1, patients suffering from interstitial cystitis may be effectively treated with modulation in accordance with the foregoing parameters at a vertebral level of from about T7-L5, inclusive, and in particular embodiments, about T7 or about T12.

Interstitial cystitis (also associated with bladder pain syndrome (BPS) or painful bladder syndrome (PBS), collectively, "IC"), is a representative condition that can result in pelvic and/or abdominal discomfort or pain and/or discomfort or pain in the bladder, which can be addressed by therapies in accordance with the presently disclosed technology. In a particular embodiment, a lead or other signal delivery device is placed epidurally at a thoracic vertebral level (e.g., T7 or perhaps more often, T12) or at one or more lumbar levels (L1-L5) and high frequency modulation signals are applied to the neural tissue in accordance with the parameters described above in the context of the present technology. The lead or other signal delivery device(s) can be implanted using an antegrade approach, e.g., toward the patient's head. Accordingly, the implanted signal delivery device can be located caudal to the signal delivery device. In a particular embodiment, a single lead is implanted at or close to the patient's axial midline to achieve bilateral pain relief.

In another embodiment, the lead or other signal delivery device is applied in a retrograde approach and/or is positioned at sacral levels (e.g., S2-S4) to achieve relief from IC pain. It is expected that the antegrade approach can provide one or more of several advantages compared with the retrograde approach. For example, the antegrade approach is typically simpler, easier and/or less complex to implement than the retrograde approach. It is expected that placing the signal delivery device (e.g., a single lead) at thoracic vertebral levels is more likely to produce bilateral effects than a lead placed at sacral levels, and can accordingly produce broader pain relief with fewer contacts, leads, and/or other devices.

In still further embodiments, modulation signals in accordance with the parameters described above in the context of the present technology are applied to a patient to treat pain resulting from erythromelalgia. Such pain can result when blood vessels, typically in the extremities, are periodically blocked. In at least some instances, pain can be addressed by selecting a vertebral level or dermatome associated with the extremity. In at least some instances it is expected that modulation applied to cervical locations can produce wide-ranging pain relief from erythromelalgia, consistent with results obtained for total body pain relief. As described above, modulation in accordance with the foregoing parameters may also be applied to treat acute and/or chronic nociceptive pain. For example, modulation in accordance with these parameters can be used during surgery to supplement and/or replace anesthetics (e.g., a spinal tap). Such applications may be used for tumor removal, knee surgery, and/or other surgical techniques. Similar techniques may be used with an implanted device to address post-operative pain, and can avoid the need for topical lidocaine. In still further embodiments, modulation in accordance with the foregoing parameters can be used to address other peripheral nerves. For example, modulation can be applied directly to peripheral nerves to address phantom limb pain. In still further embodiments, the modulation signal can be applied epidurally to address phantom limb pain. In representative examples, for upper extremity phantom limb pain, the signals can be applied at cervical vertebral levels, e.g., about C2 to about C6 (or about C2 to about C4 in certain embodiments), and for lower extremity phantom limb pain, the signals can be applied at thoracic vertebral levels, e.g., T7-T10 or in particular embodiments, T8-T9.

Signal delivery devices located at particular vertebral levels may be used to treat combinations of patient indications. For example, the practitioner may implant the signal delivery device at a cervical vertebral level to treat high back pain, mid-back pain, low back pain, leg pain and/or any combination of the foregoing back and leg pain indications. In addition to or in lieu of the foregoing combinations, the cervical location of the signal delivery device can allow the practitioner to also treat other indications that are expected to respond favorably to signals delivered from a cervical vertebral level. As shown in Table 1, such indications can include, but are not limited to, headache pain, facial pain, neck pain, brachial plexus pain, shoulder pain, elbow pain, fibromyalgia, myofascial pain, phantom limb pain, wrist pain, hand pain, chest wall pain, abdominal pain, groin pain, pelvic pain, and/or hip pain. In another example, electrodes positioned at a vertebral level of from about C4 to about C5 can address migraine pain and can also address neck pain. In some instances the same electrode(s) of a signal delivery device address multiple indications. In other embodiments, the practitioner can activate different electrodes to address different locations. The electrodes can be located on a single lead or multiple leads or other signal delivery devices. An advantage of locating the electrodes for treating multiple indications on a single lead is that it reduces the overall complexity of the system and time required to implant the system in the patient.

From the foregoing, it will be appreciated that specific embodiments of the disclosure have been described herein for purposes of illustration, but that various modifications may be made without deviating from the disclosure. For example, the specific parameter ranges and indications described above may be different in further embodiments. As described above, the practitioner can avoid the use of certain procedures, (e.g., mapping, trial periods and/or current steering), but in other embodiments, such procedures may be used in particular instances. The lead described above with reference to FIGS. 9-11C can have more than two groups of contacts, and/or can have other contact spacings in other embodiments. In some embodiments, as described above, the signal amplitude applied to the patient can be constant. In other embodiments, the amplitude can vary in a preselected manner, e.g., via ramping up/down, and/or cycling among multiple amplitudes. The signal delivery elements can have an epidural location, as discussed above with regard to FIG. 1B, and in other embodiments, can have an extradural location. In particular embodiments described above, signals having the foregoing characteristics are expected to provide therapeutic benefits for patients having low back pain and/or leg pain, when stimulation is applied at vertebral levels from about T9 to about T12. In at least some other embodiments, it is believed that this range can extend from about T5 to about L1.

Certain aspects of the disclosure described in the context of particular embodiments may be combined or eliminated in other embodiments. For example, as described above, the trial period, operating room mapping process, and/or external modulator may be eliminated or simplified in particular embodiments. Therapies directed to particular indications may be combined in still further embodiments. Further, while advantages associated with certain embodiments have been described in the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein. The following examples provide additional embodiments of the disclosed technology.

We claim:

1. A method of treating a neck or brachial plexus pain indication, exclusive of neck or brachial plexus pain associated with total body pain, comprising:
    configuring a signal generator to generate and deliver a neck or brachial plexus pain therapy signal to a target location, wherein the target location is a cervical vertebral location between C2-C6, inclusive, via one or more implanted signal delivery devices coupled to the signal generator,
    wherein at least a portion of the therapy signal is at a frequency in a frequency range of 1.5 kHz to 100 kHz, includes pulses with a pulse width in a pulse width range of 10 microseconds to 333 microseconds, and has an amplitude in an amplitude range of 0.1 mA to 20 mA, which at least partially alleviates the neck or brachial plexus pain indication, exclusive of neck or brachial plexus pain associated with total body pain, without generating paresthesia.

2. The method of claim 1, wherein the cervical vertebral location is between C3C4, inclusive.

3. The method of claim 1, wherein the neck or brachial plexus pain indication is selected from the group consisting of: cervical facet pain, cervical radiculopathy pain, myofascial pain in the cervical musculature, cervical strain pain, cervicothoracic interspinous bursitis pain, spinal stenosis pain, brachial plexopathy pain, pancoast's pain, and thoracic outlet pain.

4. The method of claim 1, wherein the frequency range is 3 kHz to 20 kHz.

5. The method of claim 1, wherein the frequency range is 5 kHz to 15 kHz.

6. The method of claim 1, wherein the one or more signal delivery devices include a percutaneous lead having one or more electrodes disposed toward a distal end of the percutaneous lead.

7. A method of treating a non-total body pain neck or brachial plexus pain indication, comprising:
    applying an electrical therapy signal to a cervical vertebral location of a patient's spinal cord, wherein the cervical vertebral location is between C2-C6, inclusive, wherein at least a portion of the electrical therapy signal (a) is at a frequency in a frequency range of from 1.5 kHz to 100 kHz, (b) includes pulses having a pulse width in a pulse width range of 10 microseconds to 333 microseconds, and (c) is at an amplitude in an amplitude range of 0.1 mA to 20 mA, and wherein the electrical therapy signal treats the neck or brachial plexus pain indication without generating paresthesia in the patient.

8. The method of claim 7, wherein the cervical vertebral location is between C3-C4, inclusive.

9. The method of claim 7, wherein the neck or brachial plexus pain indication is selected from the group consisting of: cervical facet pain, cervical radiculopathy pain, myofascial pain in the cervical musculature, cervical strain pain, cervicothoracic interspinous bursitis pain, spinal stenosis pain, brachial plexopathy pain, pancoast's pain, and thoracic outlet pain.

10. The method of claim 7, wherein the frequency range is 3 kHz to 20 kHz.

11. The method of claim 7, wherein the frequency range is 5 kHz to 15 kHz.

12. The method of claim 7, further comprising programming the signal generator to generate the electrical therapy signal.

13. The method of claim 7, wherein the electrical therapy signal is applied via one or more implanted signal delivery devices coupled to an implanted signal generator, wherein the signal generator is programmed with instructions that, when executed, treat the neck or brachial plexus pain indication by generating the electrical therapy signal and delivering the electrical therapy signal to the cervical vertebral location.

14. The method of claim 13, wherein the one or more signal delivery devices include a percutaneous lead having one or more electrodes disposed toward a distal end of the percutaneous lead.

15. The method of claim 7, wherein the frequency range is 1.5 kHz to 50 kHz.

16. The method of claim 7, wherein the frequency range is 3 kHz to 10 kHz.

17. The method of claim 7, wherein the frequency is 10 kHz.

18. The method of claim 7, wherein the portion of the electrical therapy signal is a biphasic square wave.

19. The method of claim 7, wherein the pulse width range is 25 microseconds to 166 microseconds.

20. The method of claim 7, wherein the pulse width range is 30 microseconds to 35 microseconds.

21. The method of claim 7, wherein the frequency range is 5 kHz to 15 kHz, the pulse width range is 30 microseconds to 35 microseconds, and the amplitude range is 0.5 mA to 10 mA.

22. A neck or brachial plexus pain treatment system for treating a nontotal body pain neck or brachial plexus pain indication, comprising:
a spinal cord modulation system having
at least one signal delivery device configured to be implanted proximate to a cervical vertebral location of a patient's spinal cord, wherein the cervical vertebral location is between C2C6, inclusive, and
a signal generator programmed with instructions that, when executed, treat the neck or brachial plexus pain indication by generating and delivering a nonparesthesiagenerating electrical therapy signal to the cervical vertebral location, via the at least one signal delivery device,
wherein at least a portion of the electrical therapy signal (a) is at a frequency in a frequency range of 1.5 kHz to 100 kHz, (b) includes pulses having a pulse width in a pulse width range of 10 microseconds to 333 microseconds, and (c) is at an amplitude in an amplitude range of 0.1 mA to 20 mA.

23. The system of claim 22, wherein the cervical vertebral location is between C3-C4, inclusive.

24. The system of claim 22, wherein the neck or brachial plexus pain indication is selected from the group consisting of: cervical facet pain, cervical radiculopathy pain, myofascial pain in the cervical musculature, cervical strain pain, cervicothoracic interspinous bursitis pain, spinal stenosis pain, brachial plexopathy pain, pancoast's pain, and thoracic outlet pain.

25. The system of claim 22, wherein the frequency range is from 3 kHz to 20 kHz.

26. The system of claim 22, wherein the frequency range is from 5 kHz to 15 kHz.

27. The system of claim 22, wherein the at least one signal delivery device includes a percutaneous lead having one or more electrodes disposed toward a distal end of the percutaneous lead.

28. The system of claim 22, wherein the electrical therapy signal includes one or more pulses with a pulse width between 30 microseconds and 35 microseconds.

29. The system of claim 22, wherein the electrical therapy signal includes one or more pulses with a pulse width between 25 microseconds and 166 microseconds.

* * * * *

UNITED STATES PATENT AND TRADEMARK OFFICE
CERTIFICATE OF CORRECTION

| | | |
|---|---|---|
| PATENT NO. | : 9,278,215 B2 | Page 1 of 2 |
| APPLICATION NO. | : 13/831241 | |
| DATED | : March 8, 2016 | |
| INVENTOR(S) | : James R. Thacker et al. | |

It is certified that error appears in the above-identified patent and that said Letters Patent is hereby corrected as shown below:

On the title page,

Item (57), in column 2, in "Abstract", line 2, delete "affects" and insert -- effects --, therefor.

On the page 4, in column 1, under "Other Publications", line 4, delete "Sterotactic" and insert -- Stereotactic --, therefor.

On the page 4, in column 2, under "Other Publications", line 36, delete "Offical" and insert -- Official --, therefor.

On the page 5, in column 1, under "Other Publications", line 33, delete "Neurosco," and insert -- Neurosci, --, therefor.

On the page 5, in column 1, under "Other Publications", line 55, delete "Neurmodulation" and insert -- Neuromodulation --, therefor.

On the page 5, in column 2, under "Other Publications", line 71, delete "Neurmodulation" and insert -- Neuromodulation --, therefor.

In the specification,

In column 25, lines 48-49, delete "cevicogenic" and insert -- cervicogenic --, therefor.

In column 28, line 32, delete "midaxillery" and insert -- midaxillary --, therefor.

In column 29, line 62, delete "e.g," and insert -- e.g., --, therefor.

In column 30, line 54, delete "Dematome" and insert -- Dermatome --, therefor.

In column 31, line 50, delete "Fascitis" and insert -- Fasciitis --, therefor.

In column 31, line 54, delete "Fybromyalgia" and insert -- Fibromyalgia --, therefor.

In the claims,

In column 34, line 34, in claim 2, delete "C3C4," and insert -- C3-C4, --, therefor.

In column 34, line 56, in claim 7, after "range of" delete "from".

In column 35, line 40, in claim 22, delete "nontotal" and insert -- non-total --, therefor.

Signed and Sealed this
Sixteenth Day of August, 2016

Michelle K. Lee
*Director of the United States Patent and Trademark Office*

CERTIFICATE OF CORRECTION (continued)
U.S. Pat. No. 9,278,215 B2

In column 36, line 5, in claim 22, delete "C2C6," and insert -- C2-C6, --, therefor.

In column 36, lines 8-9, in claim 22, delete "nonparesthesiagenerating" and insert -- non-paresthesia-generating --, therefor.